United States Patent
Uchiyama et al.

(10) Patent No.: US 10,761,045 B2
(45) Date of Patent: *Sep. 1, 2020

(54) SENSOR, SENSOR SYSTEM, METHOD OF MANUFACTURING SENSOR, AND METHOD OF MEASURING CONCENTRATION OF TARGET SUBSTANCE

(71) Applicant: PHC Holdings Corporation, Tokyo (JP)

(72) Inventors: Motonori Uchiyama, Ehime (JP); Takuo Kouno, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/682,655

(22) Filed: Nov. 13, 2019

(65) Prior Publication Data

US 2020/0080956 A1   Mar. 12, 2020

Related U.S. Application Data

(63) Continuation of application No. 15/251,418, filed on Aug. 30, 2016, now Pat. No. 10,571,424, which is a
(Continued)

(30) Foreign Application Priority Data

Sep. 30, 2010   (JP) ................................. 2010-222142

(51) Int. Cl.
*G01N 27/327*   (2006.01)
*C12Q 1/00*   (2006.01)
(Continued)

(52) U.S. Cl.
CPC ......... *G01N 27/3272* (2013.01); *C12Q 1/004* (2013.01); *C12Q 1/006* (2013.01);
(Continued)

(58) Field of Classification Search
CPC .................................................. G01N 27/3272
See application file for complete search history.

(56) References Cited

U.S. PATENT DOCUMENTS

| 6,773,564 B1 | 8/2004 | Yugawa et al. |
| 9,594,044 B2 | 3/2017 | Uchiyama et al. |

(Continued)

FOREIGN PATENT DOCUMENTS

| EP | 1197749 A1 | 4/2002 |
| EP | 2028712 A2 | 2/2009 |

(Continued)

OTHER PUBLICATIONS

Brian H. Kipp, et al. Imidazole facilitates electron transfer from organic reductants, Science Direct, Bioelectrochemistry 64 (2004) 7-13.
(Continued)

*Primary Examiner* — Edward J. Schmiedel
(74) *Attorney, Agent, or Firm* — Pearne & Gordon LLP

(57) ABSTRACT

The present invention provides: a reagent composition having higher storage stability; a sensor involving the reagent composition; and others. According to the present invention, a specific heterocyclic compound is added to a reagent composition to improve the storage stability of the reagent composition and reduce the degree of fluctuation in current values in a sensor that utilizes reagent composition.

6 Claims, 10 Drawing Sheets

Related U.S. Application Data continuation of application No. 13/821,365, filed as application No. PCT/JP2011/005544 on Sep. 30, 2011, now Pat. No. 9,594,044.

(51) Int. Cl.
*C12Q 1/26* (2006.01)
*C12Q 1/32* (2006.01)

(52) U.S. Cl.
CPC .................. *C12Q 1/26* (2013.01); *C12Q 1/32* (2013.01); *G01N 2333/904* (2013.01)

(56) References Cited

U.S. PATENT DOCUMENTS

| | | | |
|---|---|---|---|
| 2003/0175841 | A1 | 9/2003 | Watanabe et al. |
| 2007/0034512 | A1 | 2/2007 | Yamaoka et al. |
| 2008/0035481 | A1 | 2/2008 | McCormack et al. |
| 2008/0213808 | A1 | 9/2008 | Knappe |
| 2009/0065356 | A1 | 3/2009 | Nakayama et al. |
| 2009/0255811 | A1 | 10/2009 | Forrow et al. |
| 2010/0038242 | A1 | 2/2010 | Mao et al. |
| 2010/0047670 | A1 | 2/2010 | Kakuta et al. |
| 2010/0248042 | A1 | 9/2010 | Nakagawa et al. |
| 2011/0039165 | A1 | 2/2011 | Sugiyama et al. |
| 2011/0143225 | A1 | 6/2011 | Nakagawa et al. |
| 2011/0180404 | A1 | 7/2011 | Miyazaki et al. |
| 2012/0152763 | A1 | 6/2012 | Takahara et al. |
| 2012/0273368 | A1 | 11/2012 | Tsukada |
| 2013/0023435 | A1 | 1/2013 | Kho et al. |
| 2013/0189720 | A1 | 7/2013 | Petisce |

FOREIGN PATENT DOCUMENTS

| | | |
|---|---|---|
| JP | 2000-171428 A | 6/2000 |
| JP | 2001-343350 A | 12/2001 |
| JP | 2006-509837 A | 3/2006 |
| JP | 2007-526474 A | 9/2007 |
| JP | 2008-206518 A | 9/2008 |
| JP | 2008-243380 A | 10/2008 |
| JP | 2009-247289 A | 10/2009 |
| WO | 2005/043146 A1 | 5/2005 |
| WO | 2007/123179 A1 | 11/2007 |
| WO | 2010/007833 A1 | 1/2010 |
| WO | 2011-078794 A1 | 6/2011 |

OTHER PUBLICATIONS

International Search Report for PCT/JP2011/005544 dated Dec. 27, 2011.

Chenas, et al., Enzymatic Oxidation of Glucose on Modified Electrodes, Institute of Biochemistry, Lithuanian SSR Academy of Sciences, Vilnius, 1980, pp. 1780-1786 (English abstract on last page).

Extended European Search Report for Application No. 11828468 dated Dec. 9, 2014.

I. Lapenaite et al., "Some quinone derivatives as redox mediators for PQQ-dependent glucose dehydrogenase", Biologija, 2004, p. 20-22.

Etsuo Watanabe et al., "Determination of Hypoxanthine is Fish Mean with an Enzyme Sensor" Journal of Food Science, vol. 48, 1983.

Machine translation of JP 2001-343350; accessed and printed Aug. 3, 2018 (Year: 2018).

Histidine; Encyclopedia Britannica, Inc.; published Feb. 16, 2012; accessed Aug. 3, 2018; https://www.britannica.com/science/histidine (Year: 2012).

Sigma-Aldrich; 5-Amino-4-imidazolecarboxamide; accessed and printed Oct. 9, 2019 (Year: 2019).

SENSOR, SENSOR SYSTEM, METHOD OF MANUFACTURING SENSOR, AND METHOD OF MEASURING CONCENTRATION OF TARGET SUBSTANCE

CROSS-REFERENCE TO RELATED APPLICATIONS

This is a continuation of U.S. patent application Ser. No. 15/251,418, filed Aug. 30, 2016, which is a continuation of U.S. patent application Ser. No. 13/821,365, filed Mar. 7, 2013, which is the national stage of PCT/JP2011/005544 filed Sep. 30, 2011, which claims priority to Japanese patent Application No. 2010-222142 filed Sep. 30, 2010.

TECHNICAL FIELD

The present invention relates to reagent compositions, sensors, sensor systems, and methods of manufacturing the sensor.

BACKGROUND ART

Sensors for detecting target substances in liquid samples have heretofore been proposed. For blood glucose sensors, one example of such sensors, the liquid sample is blood and the target substance is glucose.

Most of the blood glucose sensors proposed so far are electrochemical blood glucose sensors. The electrochemical blood glucose sensor has an enzyme and an electron acceptor. The enzyme specifically reacts with blood glucose (i.e., enzyme-substrate reaction) to oxidize the glucose. The electron acceptor is converted from the oxidized form to the reduced form by accepting the electron generated by the oxidation. The reduced form of the electron acceptor is electrochemically oxidized for instance on the electrode. The concentrations of glucose in the blood, i.e., blood glucose levels are detected based on the magnitude of a current generated by this oxidation.

In a typical sensor manufacturing process, an enzyme and an electron acceptor are applied onto a substrate by applying a reagent solution in which they are dissolved. A reagent layer forms as a result of the drying of the reagent solution. The enzyme-substrate reaction proceeds as the reagent layer dissolves into a liquid sample.

Known reagent compositions used for such a reagent solution include reagent compositions containing an oxidoreductase such as glucose dehydrogenase, an electron acceptor such as a quinone compound, and an additive such as histidine and/or imidazole (see, e.g., Patent Literatures 1, 2 and 4). Reagent compositions containing an oxidoreductase such as pyrroloquinoline quinone (PQQ)-dependent glucose dehydrogenase, and a transition metal complex having a pyridyl imidazole ligand are also known (see, e.g., Patent Literature 3). Moreover, the redox potential of a quinone compound is known to be shifted to negative potentials at a particular pH in a solution containing the quinone compound and imidazole (see, e.g., Non-Patent Literature 1).

CITATION LIST

Patent Literature

[PTL 1] Japanese Patent Application Laid-Open No. 2000-171428

[PTL 2] Japanese Patent Application Laid-Open No. 2001-343350

[PTL 3] Japanese Unexamined Patent Application Publication (Translation of PCT application) No. 2006-509837

[PTL 4] Japanese Patent Application Laid-Open No. 2009-247289

[NPL 1] Bioelectrochemistry, 64, (2004), p. 7-13

SUMMARY OF INVENTION

Technical Problem

The inventors found that there may be changes in the value of a current, generated upon application of a voltage, between before and after the reagent solution or layer has passed its storage period. Changes in the current value reduce the sensor's measurement accuracy. Thus, there still remains a room for improvement of the storage stability of the conventional reagent solution and layer.

In view of the foregoing problem pertinent in the art, the present invention aims at providing a novel reagent composition capable of limiting changes in the current value between before and after the storage period, and a sensor and a sensor system including the reagent composition.

Solution to Problem

As means of achieving the foregoing objective, the present invention provides the following reagent compositions and the like.

[1] A reagent composition including:
an oxidoreductase;
an electron acceptor; and
a heterocyclic compound represented by general formula (I), wherein the reagent composition satisfies a first requirement or a second requirement described below,

[Formula 1]

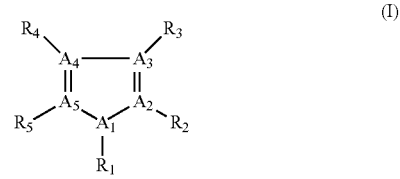

In general formula (I), $R_1$ to $R_5$ independently represent a hydrogen atom, amino group, hydroxyl group, carboxyl group, or $C_{1-12}$ hydrocarbon group; the hydrocarbon group may have at least one substituent selected from the group consisting of amino group, hydroxyl group, and carboxyl group; two or three of $A_1$ to $A_5$ represent a nitrogen atom, and the others of $A_1$ to $A_5$ represent a carbon atom; and when two of $A_1$ to $A_5$ represent a nitrogen atom, $A_1$ represents a nitrogen atom and $A_2$ and $A_5$ represent a carbon atom.

(First Requirement)
In the reagent composition according to [1], the electron acceptor is at least one quinone compound selected from the group consisting of naphthoquinone, anthraquinone, phenanthrenequinone, phenanthroline quinone, and quinone derivatives thereof.

(Second Requirement)
In the reagent composition according to [1], when the heterocyclic compound excludes histidine and two of $A_1$ to $A_5$ in general formula (I) represent a nitrogen atom, at least one of $R_1$ to $R_5$ represents a substituent other than hydrogen atom.

[2] The reagent composition according to [1], wherein the heterocyclic compound has three or more nitrogen atoms.

[3] The reagent composition according to [1] or [2], wherein in general formula (I) at least one of $R_1$ to $R_5$ represents a chain hydrocarbon group represented by $C_nH_{m-(a+b+c)}(R_6)_a(R_7)_b(R_8)_c$, where n represents a natural number of 2 or less; m represents a natural number of n+1 to 2n+1; a, b and c independently represent a natural number of n or less; and $R_6$ to $R_8$ independently represent a hydroxyl group, carboxyl group, or amino group.

[4] The reagent composition according to any one of [1] to [3], wherein the heterocyclic compound has a substituent having an amino group.

[5] The reagent composition according to any one of [1] to [4], wherein a 5-membered heteroring of the heterocyclic compound is triazole.

[6] The reagent composition according to any one of [1] to [5], wherein the reagent composition contains as the heterocylic compound at least one compound selected from the group consisting of imidazole, histamine, histidine, 2-amino-imidazole, 4,5-bis(hydroxymethyl)imidazole, 2-methylimidazole, 1,2-dimethylimidazole, 1,2,4-triazole, 3-amino-1,2,4-triazole, 4-amino-1,2,4-triazole, and 3,5-diamino-1,2,4-triazole (with the proviso that imidazole and histidine are excluded when the second requirement is satisfied).

[7] The reagent composition according to any one of [1] to [6], wherein the reagent composition contains as the heterocylic compound at least one compound selected from the group consisting of histamine, histidine, 2-amino-imidazole, 4,5-bis(hydroxymethyl)imidazole, 2-methylimidazole, 1,2-dimethylimidazole, 1,2,4-triazole, 3-amino-1,2,4-triazole, 4-amino-1,2,4-triazole, and 3,5-diamino-1,2,4-triazole (with the proviso that histidine is excluded when the second requirement is satisfied).

[8] The reagent composition according to any one of [1] to [7], wherein when the reagent composition satisfies the second requirement, the reagent composition contains an iron cyanocomplex as the electron acceptor.

[9] The reagent composition according to any one of [1] to [8], wherein when the reagent composition satisfies the second requirement, the reagent composition contains a quinone compound as the electron acceptor.

[10] The reagent composition according to any one of [1] to [9], wherein the reagent composition contains as the quinone compound either one or both of a phenanthrenequinone and a phenanthrenequinone derivative.

[11] The reagent composition according to [10], wherein the reagent composition contains as the quinone compound either one or both of 9,10-phenanthrenequinone and a 9,10-phenanthrenequinone derivative.

[12] The reagent composition according to any one of [1] to [11], wherein the quinone compound has a hydrophilic functional group.

[13] The reagent composition according to [12], wherein the quinone compound has a quinone and a substituent, and the substituent has a benzene ring which may be substituted, and the hydrophilic functional group attached to the benzene ring.

[14] The reagent composition according to [12] or [13], wherein the quinone compound has as the hydrophilic group at least one functional group selected from the group consisting of sulfo group, carboxyl group, and phosphate group.

[15] The reagent composition according to [14], wherein the quinone compound satisfies at least one of the following conditions (a) to (c): (a) the sulfo group is 1-sulfonic acid, 2-sulfonic acid, 3-sulfonic acid, 4-sulfonic acid, or 2,7-disulfonic acid; (b) the carboxyl group is 2-carboxylic acid; and (c) the phosphate group is 2-phosphoric acid.

[16] The reagent composition according to any one of [1] to [15], wherein the reagent composition contains glucose dehydrogenase as the oxidoreductase.

[17] The reagent composition according to [16], further including a coenzyme operable with the oxidoreductase.

[18] The reagent composition according to [16] or [17], wherein the oxidoreductase has PQQ dependency or FAD dependency.

[19] The reagent composition according to any one of [1] to [18], further including a water-containing liquid as a medium.

[20] A sensor including:
a sample chamber configured to receive therein a liquid sample;
at least one pair of electrodes disposed in the sample chamber; and
a reagent layer formed of the reagent composition according to any one of [1] to [19], the reagent layer being disposed in the sample chamber so as to be in contact with both electrodes of the at least one pair of electrodes.

[21] A sensor system including:
the sensor according to [20];
a measurement section that measures a current value between the electrodes of the at least one pair of electrode; and
a calculation section that calculates a concentration of a target substance in the liquid sample based on a measurement result obtained by the measurement section.

[22] A method of manufacturing a sensor, including:
(a) providing at least one pair of electrodes on a substrate;
(b) applying on the substrate the reagent composition according to any one of [1] to [19] so as to be in contact with both electrodes of the at least one pair of electrodes; and
(c) drying the reagent composition applied in the step (b).

[23] A method of measuring a concentration of a target substance, including:
(a) bringing a reagent composition containing at least an electron acceptor and an enzyme into contact with a liquid sample;
(b) detecting a current generated in the step (a); and
(c) measuring the concentration of the target substance based on a detection result obtained in the step (b),
wherein the reagent composition according to any one of [1] to [19] is used as the reagent composition.

Advantageous Effects of Invention

The reagent composition of the claimed invention limits, by means of a heterocyclic compound, changes in the current value between before after the storage period. The reagent composition is advantageously used for a reagent layer of a sensor.

DESCRIPTION OF EMBODIMENTS

<1. Reagent Composition>

Figure 1:
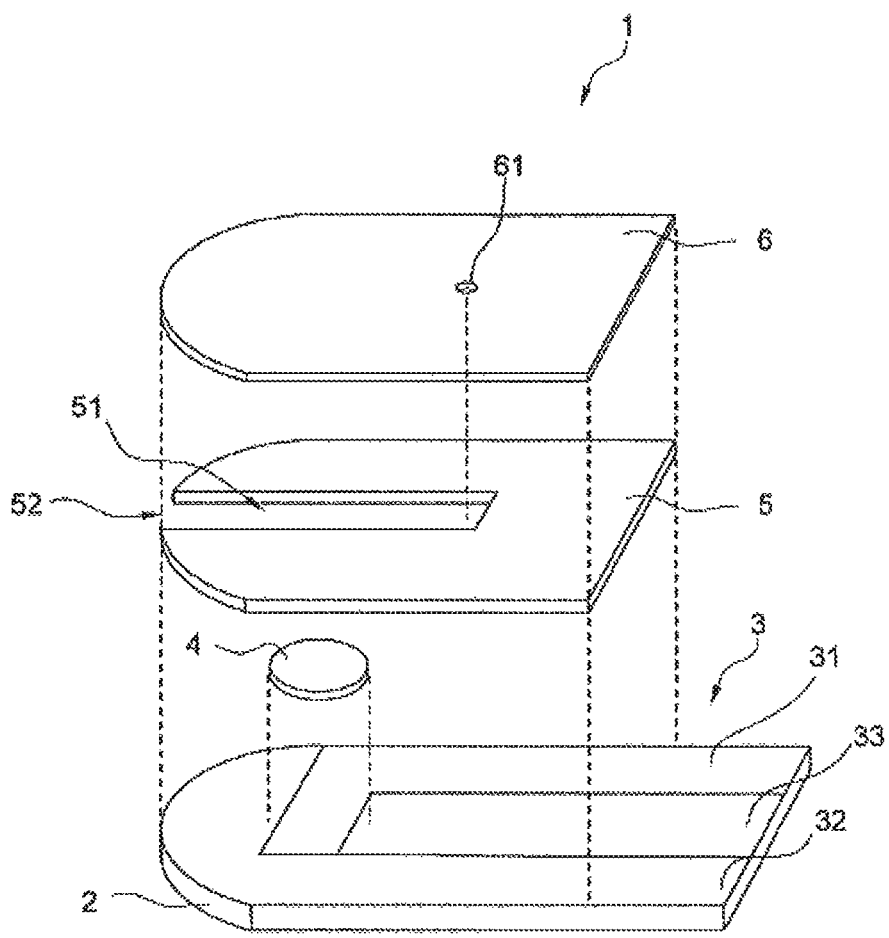
FIG. 1 is an exploded perspective view illustrating a schematic configuration of a sensor.

The reagent composition contains a heterocyclic compound, an electron acceptor, and an oxidoreductase.

(1-1) Heterocyclic Compound

As the heterocyclic compound, the reagent composition can contain at least one compound selected from the compounds described below. The heterocyclic compound is represented by formula (I) illustrated below. The heterocyclic compound represented by formula (I) can limit the positive shift of the oxidation potential of an electron acceptor under the presence of an oxidoreductase.

[Formula 2]

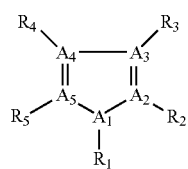

(I)

In formula (I), $R_1$ to $R_5$ independently represent a hydrogen atom, amino group, hydroxyl group, carboxyl group, or $C_{1-12}$ hydrocarbon group. $R_1$ to $R_5$ preferably represent a substituent that can ensure the water solubility of the heteroring. When $R_1$ to $R_5$ represent a hydrocarbon group free from any attached group (i.e., at least one substituent selected from the group consisting of amino group, hydroxyl group, and carboxyl group, as described below), $R_1$ to $R_5$ preferably represent a $C_{1-4}$ hydrocarbon group; when $R_1$ to $R_5$ represent a hydrocarbon group having an attached group, $R_1$ to $R_5$ preferably represent a $C_{1-12}$ hydrocarbon group.

In formula (I), the hydrocarbon group may have at least one substituent selected from the group consisting of amino group, hydroxyl group, and carboxyl group. The hydrocarbon group may be either a chain or cyclic hydrocarbon. The chain hydrocarbon group may be branched or linear. The chain hydrocarbon group may be a saturated or unsaturated hydrocarbon group.

For example, in general formula (I), at least one of $R_1$ to $R_5$ may represent a chain hydrocarbon group represented by $C_nH_{m-(a+b+c)}(R_6)_a(R_7)_b(R_8)_c$, where n represents a natural number of 2 or less; m represents a natural number of n+1 to 2n+1; a, b and c independently represent a natural number of n or less; and $R_6$ to $R_8$ independently represent a hydroxyl group, carboxyl group, or amino group. For a saturated hydrocarbon group, m is represented as 2n+1.

As a specific example, $R_1$ to $R_5$ may independently represent a hydrogen atom, —$NH_2$, —$CH_3$, —$CH_2OH$, —$C_2H_4NH_2$, or —$CH_2$—$CH(NH_2)$—COOH.

In formula (I), two or three of $A_1$ to $A_5$ may represent a nitrogen atom, and the others may represent a carbon atom. More specifically, the heterocyclic compound may be imidazole or triazole which may have a substituent. When two of $A_1$ to $A_5$ represent a nitrogen atom, $A_1$ represents a nitrogen atom and $A_2$ and $A_5$ represent a carbon atom. When two of $A_1$ to $A_5$ represent a nitrogen atom, at least one of $R_1$ to $R_5$ preferably represents a substituent other than hydrogen atom.

The heterocyclic compound may contain at least three nitrogen atoms. Namely, the total number of nitrogen atoms contained in the heteroring and substituent(s) may be 3 or more. In this case, when the number of nitrogen atoms in the heteroring is 2, one or more substituents are attached to the heteroring, with the total number of nitrogen atoms contained in all of the substituent being 1 or more. On the other hand, when the number of nitrogen atoms contained in the heteroring is 3, the heteroring may not have any substituent or can have a substituent which may contain nitrogen atom(s). Regardless of the number of nitrogen atoms contained in the heteroring, the heterocyclic compound may have a nitrogen-free substituent.

The heteroring may be a 5-membered ring, more specifically may be a 5-membered ring containing two or more nitrogen atoms, preferably two or three nitrogen atoms. The 5-membered ring may be, for example, imidazole or triazole. As the triazole, 1,2,4-triazole is preferable.

As one example of a nitrogen-containing substituent, an amino group-containing substituent can be exemplified. The amino group-containing substituent can be an amino group itself and a hydrocarbon group substituted with one or more amino groups. The heterocyclic compound having an amino group exhibits the effect of limiting the positive shift of the oxidation potential of an electron acceptor not only under the presence of an oxidoreductase but also under high-temperature/humidity conditions. Thus, the heterocyclic compound having an amino group also exhibits superior environmental stability.

Examples of the heterocyclic compound represented by formula (I) include imidazole, histamine, histidine, 2-aminoimidazole, 4,5-bis(hydroxymethyl)imidazole, 2-methylimidazole, 1,2-dimethylimidazole, 1,2,4-triazole, 3-amino-1,2,4-triazole, 4-amino-1,2,4-triazole, and 3,5-diamino-1,2,4-triazole. These heterocyclic compounds are preferable from the perspective of limiting the positive shift of the oxidation potential of an electron acceptor.

Among the aforementioned heterocyclic compounds, histamine, histidine, 2-amino-imidazole, 4,5-bis(hydroxymethyl)imidazole, 2-methylimidazole, 1,2-dimethylimidazole, 1,2,4-triazole, 3-amino-1,2,4-triazole, 4-amino-1,2,4-triazole, and 3,5-diamino-1,2,4-triazole are more preferable because of their superior environmental stability.

(1-2) Electron Acceptor

An electron acceptor may also be referred to as an electron transfer substance or a mediator. An electron acceptor can be reversely converted into the oxidized form or reduced form. An electron acceptor can mediate the transfer of electrons between substances, either directly or in cooperation with another electron acceptor. Either one or more types of electron acceptor may be used.

Examples of the electron acceptor include quinone compounds, iron cyanocomplexes, phenazine methosulfate and derivatives thereof, methylene blue and derivatives thereof, and ferrocene and derivatives thereof.

Examples of the iron cyanocomplexes include ferricyanide salts. Examples of the ferricyanide salts include potassium ferricyanide.

The quinone compound is a quinone-containing compound. The quinone compound can be a quinone or a quinone derivative. Examples of the quinone derivative includes quinones having various functional groups (or substituents) attached.

Examples of the quinone in the quinone compound include (a) benzoquinone, (b) naphthoquinone, (c) anthraquinone, (d) phenanthrenequinone, and (e) phenanthrolinequinone. A specific example of phenanthrenequinone is 9,10-phenanthrenequinone. Specific example(s) of the structural formula of each quinone are illustrated below. Note that the quinones encompass their isomers though such isomers are not designated in the structural formulas illustrated below.

[Formula 3]

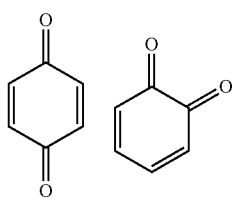

(a)

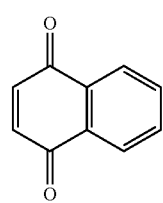

(b)

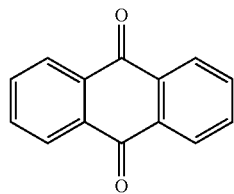

(c)

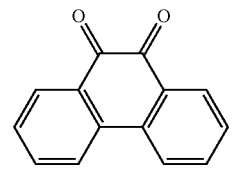

(d)

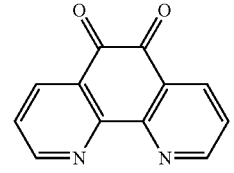

(e)

One quinone derivative may have two or more types of functional group. One example of an attached functional group (i.e., substituent) to the quinone derivative is a hydrophilic functional group. Examples of the hydrophilic functional group include sulfo group ($-SO_3H$), carboxyl group ($-COOH$), and phosphate group ($-PO_4H_2$). Sulfo group, carboxyl group, and phosphate groups can also be their salt (e.g., sodium salt, potassium salt, and calcium salt).

The substituent may be a $C_{1-16}$ hydrocarbon group which may have a substituent. The aforementioned hydrophilic functional groups are suitable as the substituents to be attached to the hydrocarbon group. Examples of the hydrocarbon group include alkyl groups such as methyl group and ethyl group; vinyl group; and aryl groups such as phenyl group, naphthyl group, phenanthryl group, anthryl group, and pyrenyl group.

The quinone derivative may have a substituent having a benzene ring. The aforementioned hydrophilic functional groups (including their salts) may be attached to the benzene ring of the substituent. In other words, the hydrophilic functional groups may be attached to the quinone via the benzene ring.

For example, the aforementioned quinone compounds may satisfy at least one of the following conditions (a) to (c): (a) the aforementioned sulfo group is 1-sulfonic acid, 2-sulfonic acid, 3-sulfonic acid, 4-sulfonic acid, or 2,7-disulfonic acid; (b) the aforementioned carboxyl group is 2-carboxylic acid; and (c) the aforementioned phosphate group is 2-phosphoric acid. For example, at least one of the following substituents may be attached to the aforementioned quinones (a) to (e). Note that the following "substituents" can be their regioisomers.

[Formula 4]

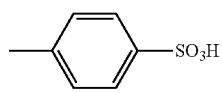

(G1)

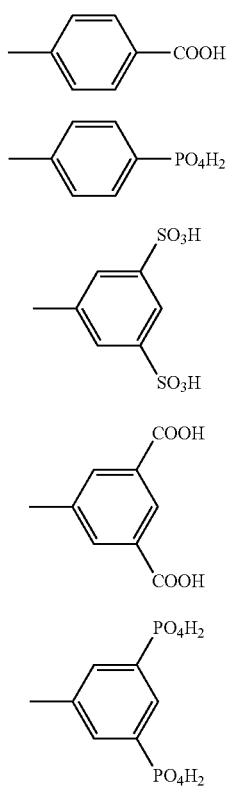

(G2), (G3), (G4), (G5), (G6)

In the substituent, two or more identical functional groups may be attached to a single benzene ring, or two or more types of functional group may be attached to a single benzene ring.

Furthermore, one or more other atoms may be interposed between the benzene ring and the aforementioned hydrophilic functional group. Examples of such electron acceptors include Compounds A, B, H', I, I', and J illustrated below. The reaction schemes illustrated below include a synthesis scheme for each compound, where p-TsOH stands for p-toluenesulfonic acid.

Compound A is prepared by refluxing 9,10-phenanthrenequinone in 65% nitric acid. Compound B is prepared by reducing Compound A with sodium thiosulfate under the presence of sodium hydroxide. Compound B turns into Compound C by converting it into a diazonium salt by treatment with sodium nitrite followed by substitution of the amino group with iodine. Compound C turns into Compound D by substituting iodine with lithium by treatment with butyl lithium followed by reaction with 2-isopropoxy-4,4,5,5-tetramethyl-1,3,2-dioxaborolane. Compound H' is prepared by reaction of Compound D with sodium 4-iodobenzene sulfonate. Compound I is prepared by reaction of Compound D with sodium 4-iodobenzoate. Compound J is prepared by reaction of Compound D with disodium 5-iodoisophthalate. Compound I' is prepared by the condensation reaction of Compound I with aminoethanesulfonic acid. The substituents in Compound I' include a benzene ring, a sulfo group, and an aminocarboxyl moiety (—CONH—) between the sulfo group and benzene ring.

[Formula 5]

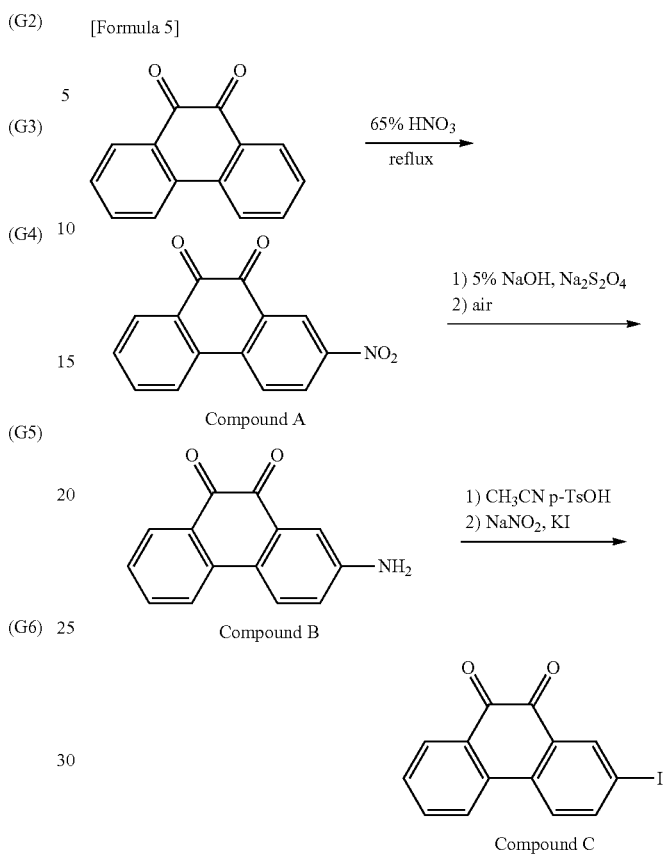

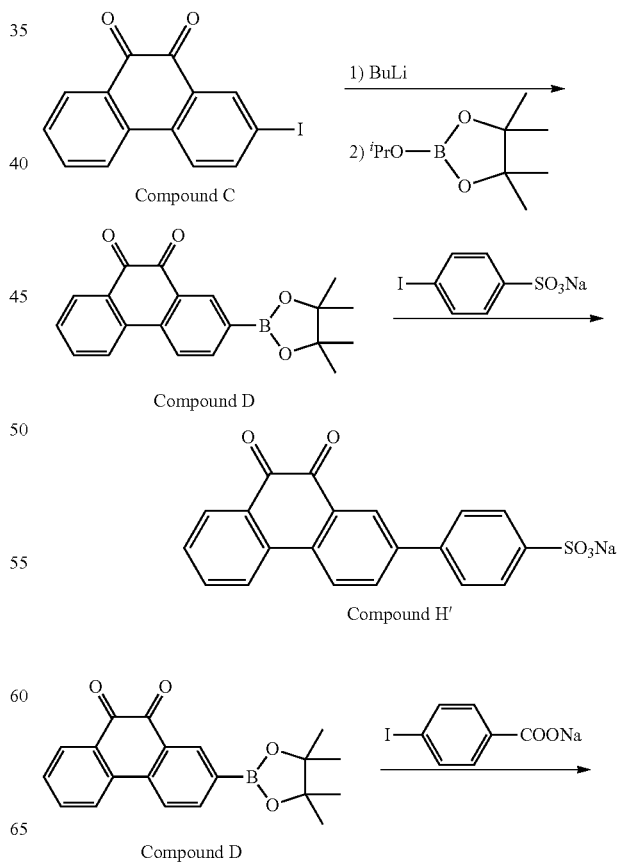

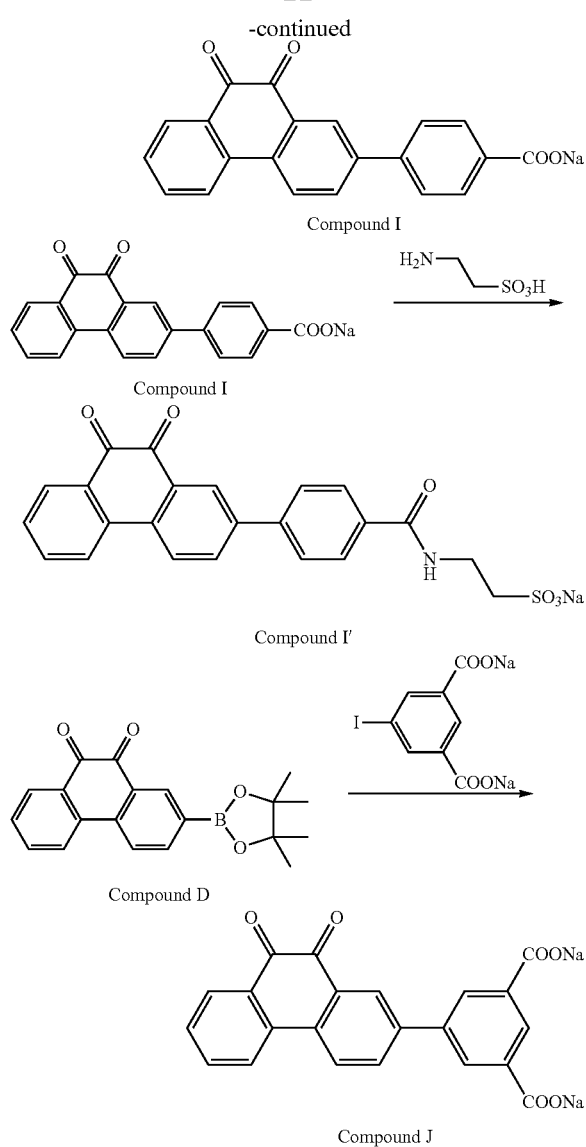

Solubilities in water of Compounds A, B, H', I, I' and J and disodium 9,10-phenanthrenequinone 2,7-disulfonate are given in Table 1.

TABLE 1

| Mediator | Solubility in water |
| --- | --- |
| Disodium 9,10-phenanthrenequinone-2,7-disulfonate | ≥200 mM |
| Compound A | 1 mM |
| Compound B | 1 mM |
| Compound H' | 20 mM |
| Compound I | 5 mM |
| Compound I' | 20 mM |
| Compound J | 50 mM |

Redox potentials of these compounds are as given in Table 2. Redox potential (EO') was calculated in the following procedure. Specifically, cyclic voltammetry using Ag|AgCl as the reference electrode was performed under the same conditions as those in Examples to be described later. Redox potential (EO') was found as an average of the potential value at the peak oxidation current (Eox) and the potential value at the peak reduction current (Ered), i.e., [(Ered+Eox)/2].

As indicated in Table 2, these compounds exhibited relatively low redox potentials. Electron acceptors that exhibit such low redox potentials are advantageously used for sensors.

TABLE 2

| Mediator | Ered (V) | Eox (V) | EO' (V) [(Ered + Eox)/2] |
| --- | --- | --- | --- |
| Sodium 9,10-phenanthrenequinone-2-sulfonate | −0.18 | −0.12 | −0.15 |
| Disodium 9,10-phenanthrenequinone 2,7-disulfonate | −0.18 | −0.06 | −0.12 |
| Compound A | −0.13 | −0.10 | −0.12 |
| Compound B | −0.23 | −0.19 | −0.21 |
| Compound H' | −0.21 | −0.14 | −0.18 |
| Compound I | −0.22 | −0.14 | −0.18 |
| Compound I' | −0.22 | −0.14 | −0.18 |
| Compound J | −0.23 | −0.15 | −0.19 |

There are no particular limitations on the positions of the substituents on the quinone. For example, for 9,10-phenanthrenequinone, at least one of the 1-, 2-, 3-, 4-, and 7-positions is suitable substituent position.

As a specific quinone derivative, the reagent composition may contain at least one compound selected from the group consisting of 9,10-phenanthrenequinone-2-sulfonic acid, 9,10-phenanthrenequinone-1-sulfonic acid, 9,10-phenanthrenequinone-3-sulfonic acid, 9,10-phenanthrenequinone-4-sulfonic acid, 9,10-phenanthrenequinone-2,7-disulfonic acid, 9,10-phenanthrenequinone-2-carboxylic acid, and 9,10-phenanthrenequinone-2-phosphoric acid.

Any of the processes known in the art can be used as the process for producing the quinone compound. Quinones have been used in the fields of medicine, agrochemicals, and industry. Quinones can be prepared for instance from aromatic hydrocarbons. More specifically, anthraquinone can be easily prepared by the oxidation of anthracene. The method of preparing a quinone compound having a hydrophilic functional group may include the step of introducing the hydrophilic functional group into the quinone. An exemplary method of adding a sulfo group as a hydrophilic functional group to a quinone involves, for example, reacting the quinone with fuming sulfuric acid.

The volatility of quinone compounds having a hydrophilic functional group tends to be lower than that of quinones having no hydrophilic functional group. Thus, when a hydrophilic functional group is attached to a quinone compound, the quinone compound advantageously functions as an electron acceptor when it is contained reagent layer 4.

(1-3) Enzyme

The reagent composition may contain one or more types of enzyme. An oxidoreductase is used, which contains an oxidase and a dehydrogenase. As to examples of the oxidoreductase, when the target substrate is glucose, glucose oxidase or glucose dehydrogenase is preferable; when the target substance is lactic acid, lactic acid oxidase or lactic acid dehydrogenase is preferable; when the target substance is cholesterol, cholesterol esterase or cholesterol oxidase is preferable; when the target substance is an alcohol, alcohol oxidase is preferable; and when the target substance is bilirubin, bilirubin oxidase is preferable.

The reagent composition may contain a coenzyme operable with the enzyme. There are no particular limitations on the enzyme as to its coenzyme dependence. For example, the enzyme may have dependence on such a coenzyme as nicotinamide adenine dinucleotide (NAD), nicotinamide adenine dinucleotide phosphate (NADP), pyrroloquinoline quinone (PQQ), or flavin adenine dinucleotide (FAD).

The coenzyme for the enzyme is preferably FAD or PQQ. In enzymes operable with these coenzymes, the coenzyme is either bound to or contained in the enzyme protein. This eliminates the need to add the coenzyme separately from the enzyme. As a result, the sensor configuration, manufacturing process, and measurement process are all simplified.

On the other hand, when using NAD- and NADP-dependent enzymes, coenzyme NAD and NADP that function without being bound to the enzyme protein may be added. For example, the enzyme may be an FAD-dependent oxidase; NAD-dependent, PQQ-dependent, or FAD-dependent dehydrogenase, or the like. Specific examples of the oxidase and dehydrogenass are as given above.

(1-4) Requirements of Combinations

By combining the aforementioned heterocyclic compounds with the aforementioned electron acceptors, every heterocyclic compound at least exerts the aforementioned effect of limiting the positive shift of the oxidation potential of the electron acceptor. Among the possible combinations, the present invention satisfies either the first requirement or second requirement described below. Under the first requirement, there are no particular limitations on the oxidoreductase and the compound represented by general formula (I). Under the second requirement, there are no particular limitations on the oxidoreductase and the electron acceptor.

(First Requirement)

The aforementioned electron acceptor is at least one quinone compound selected from the group consisting of naphthoquinone, anthraquinone, phenanthrene quinone, phenanthroline quinone, and quinone derivatives thereof.

(Second Requirement)

When the aforementioned heterocyclic compound excludes histidine and two of $A_1$ to $A_5$ in general formula (I) represent a nitrogen atom, at least one of $R_1$ to $R_5$ represents a substituent other than hydrogen atom.

(1-5) Additional Components

The reagent composition may contain additional component(s) in addition to the heterocyclic compound, oxidoreductase, and electron acceptor. The additional components are preferably compounds that can increase: the storage stability of the enzyme or electron acceptor; the reactivity of the enzyme to a target substance; the response to the target substance; or the linearity of the response current to target substance concentration, when the reagent composition is for instance used for sensors.

Examples of the additional components include sugar alcohols. Examples of the sugar alcohols include linear chain polyalcohols and cyclic sugar alcohols, such as sorbitol, maltitol, xylitol, mannitol, lactitol, reduced paratinose, arabinitol, glycerol, ribitol, galactitol, sedoheptitol, perseitol, volemitol, styracitol, polygalitol, iditol, talitol, allitol, isylitol, hydrogenated starch, and isylitol. Examples of the additional components also include stereoisomers, substituted analogues and derivatized analogues of these sugar alcohols.

Examples of the additional components also include organic acids or organic acid salts having at least one amino group or carbonyl group in the molecule thereof. Examples of such organic acids and salts thereof include amino acids, substituted analogues thereof, derivatized analogues thereof, and salts of the foregoing. Examples of the amino acids include glycine, alanine, valine, leucine, isoleucine, serine, threonine, methionine, asparagine, glutamine, arginine, lysine, phenylalanine, proline, sarcosine, betaine, and taurine. Among the aforementioned amino acids and salts and the like thereof, glycine, serine, proline, threonine, lysine, and taurine are suitable because of their higher effect of inhibiting crystallization. These compounds are preferable from the perspective of improving the sensor's response.

The reagent composition may further contain a buffer agent. For example, the reagent composition may further contain a sodium phosphate such as $NaH_2PO_4$ or $Na_2HPO_4$, a potassium phosphate such as $KH_2PO_4$ or $K_2HPO_4$, N-(2-acetamide)-2-aminoethanesulfonic acid (ACES), tris(hydroxymethyl) aminomethane (Tris), and/or the like.

The buffer agent can include a buffer solution. Namely, the reagent composition may contain a buffer solution such as a sodium phosphate buffer solution, an ACES buffer solution, or a Tris buffer solution.

The reagent composition may also contain additives, e.g., either one or both of trisodium citrate and calcium chloride ($CaCl_2$). When the reagent composition is used for sensors, trisodium citrate and calcium chloride can enhance the linearity of the sensor's response current to glucose concentration.

The reagent composition may also contain a hydrophilic polymer. When the reagent composition is used to form a reagent layer of a sensor, the addition of a hydrophilic polymer in the reagent composition prevents the reagent layer from being peeled from the electrode surface. Hydrophilic polymers also offer the effect of preventing cracking in the surface of the reagent layer. Examples of the hydrophilic polymers include carboxymethyl cellulose, hydroxyethyl cellulose, hydroxypropyl cellulose, methyl cellulose, ethyl cellulose, ethyl hydroxyethyl cellulose, carboxymethylethyl cellulose, polyethylene glycol, polyvinylpyrrolidone, polyvinyl alcohol, polyamino acids such as polylysine, polystyrene sulfonate, gelatin and derivatives thereof, polyacrylic acid and salts thereof, polymethacrylic acid and salts thereof, starch and derivatives thereof, maleic anhydride polymer and salts thereof, and agarose gel and derivatives thereof.

(1-6) Form of Reagent Composition

The reagent composition may be in liquid or solid form. When the reagent composition is liquid, examples of the medium contained in the reagent composition include water (including buffer solutions), alcohols (including ethanol, methanol, propanol and the like), and organic solvents (including benzene, toluene, xylene and the like). The reagent composition in liquid form may be referred to as a "reagent solution." The medium is preferably water from the perspective of compatibility with biological samples.

(1-7) Amounts of Components

The concentration of the heterocyclic compound in the reagent solution is preferably 0.001 mM or more, more preferably 0.01 mM or more, still more preferably 0.1 mM or more, and further preferably 1 mM or more. The concentration of the heterocyclic compound in the reagent solution can be set to 10 mM or less, 5 mM or less, or 4 mM or less.

The molecular ratio of electron acceptor to heterocyclic compound is preferably 10,000:1 to 1:1,000, more preferably 1,000:1 to 1:100, and still more preferably 100:1 to 1:10.

The amount of heterocyclic compound per unit of enzyme is preferably 0.005 to 250 nmol, and more preferably 0.1 to 40 nmol.

The amount of electron acceptor per unit of enzyme is preferably 0.05 to 2,500 nmol, and more preferably 1 to 400 nmol.

It should be noted that in the present invention, some diamine compounds offer the effect of limiting the positive shift of the oxidation potential of an electron acceptor under the presence of an oxidoreductase, as with the aforementioned heterocyclic compounds used in the present invention. In the present invention, such diamine compounds can be used instead of the heterocyclic compounds. Examples of such diamine compounds include ethylenediamine, ornithine, lysine, and arginine.

<2. Sensor>

A sensor of the claimed invention includes a sample chamber configured to receive therein a liquid sample; at least one pair of electrodes disposed in the sample chamber; and a reagent layer disposed in the sample chamber so as to be in contact with both electrodes of the at least one pair of electrodes. The reagent layer is formed of the aforementioned reagent composition of the claimed invention. The sensor of the claimed invention can be configured in the same manner as any of the known sensors for electrochemically detecting target substances in liquid samples, except that the reagent layer is formed using the reagent composition of the claimed invention.

The sensor of the claimed invention can be manufactured by the method including: (a) providing at least one pair of electrodes on a substrate; (b) applying on the substrate the aforementioned reagent composition of the claimed invention so as to be in contact with both electrodes of the at least one pair of electrodes; and (c) drying the reagent composition applied in the step (b).

The sensor manufacturing method of the claimed invention can be effected in the same manner as any of the known methods of manufacturing a sensor for electrochemically detecting target substances in liquid samples, except that the reagent composition of the claimed invention is used to form the reagent layer.

The sensor of the claimed invention includes the aforementioned reagent composition of the claimed invention. The reagent composition contains the aforementioned heterocyclic compound. When some components in the dried reagent layer slightly dissolve by exposing the reagent layer to moisture in the atmosphere, the concentrations of other components in the reagent layer become temporarily high, which may cause unwanted enzyme deactivation. By contrast, by employing the reagent composition containing the aforementioned heterocyclic compound, the sensor and sensor manufacturing method of the claimed invention can prevent enzyme deactivation caused by concentration fluctuations of components in the composition.

A sensor of the claimed invention will now be described with reference to an exemplary sensor illustrated in the accompanying drawings.

(2-1) Schematic Configuration of Sensor

Sensor 1 illustrated in FIG. 1 is an example of a sensor for detecting and/or quantifying a target substance in a liquid sample. As illustrated in FIG. 1, sensor 1 includes substrate 2, conductive layer 3, reagent layer 4, spacer 5, and cover 6.

(2-2) Substrate

As illustrated in FIG. 1, substrate 2 is a plate-shaped member. Substrate 2 has an electrical insulation property. Examples of the constituent material of substrate 2 include resins such as polyethylene terephthalate, vinyl polymers, polyimides, polyesters, and styrenics; glass; and ceramics.

Substrate 2 is not limited to any specific dimensions. For example, the width of substrate 2 is preferably 3 to 20 mm, and more preferably 5 to 10 mm. The length of substrate 2 is preferably 20 to 40 mm. The thickness of substrate 2 is preferably 0.1 to 1 mm. The width, length, and thickness of substrate 2 are all preferably within these ranges.

(2-3) Conductive Layer

As illustrated in FIG. 1, conductive layer 3 is formed in a substantially uniform thickness over substrate 2. Conductive layer 3 includes three electrodes 31 to 33. In some cases, electrode 31 is called a working electrode, electrode 32 a counter electrode, and electrode 33 a sensing electrode. Electrode 33 may not be provided. Alternatively, conductive layer 3 may be composed of four electrodes: the aforementioned three electrodes plus a Hct electrode (not illustrated) for measuring hematocrit levels.

A portion of each of electrodes 31 to 33 is disposed so as to face capillary 51. The other portion of electrodes 31 to 33 is arranged to be exposed, i.e., not covered by spacer 5 and cover 6, at the opposite end from inlet 52 of sensor 1. These exposed portions function as leads. That is, these exposed portions correspond to connection portions that receive the application of a voltage from measurement device 101 and transmit a current to measurement device 101.

Each electrode may be formed by: patterning by printing a conductive material; or covering substrate 2 with a conductive material, followed by formation of a non-conductive track by laser ablation or other technique. For example, conductive layer 3 can be formed by sputtering palladium onto substrate 2, followed by formation of a non-conductive track by laser ablation. The non-conductive track preferably has a width of 0.01 to 0.5 mm, and more preferably 0.05 to 0.3 mm.

There are no particular limitations on the constituent material of conductive layer 3, as long as it is a conductive material (conductive substance). Examples of the conductive material include inorganic conductive substances such as metals, metal mixtures, alloys, metal oxides, and metal compounds; organic conductive substances such as hydrocarbon conductive polymers, and heteroatom-containing conductive polymers; and combinations of the foregoing. The constituent material of conductive layer 3 is preferably palladium, gold, platinum, carbon or the like, with palladium being particularly preferable.

The thickness of conductive layer 3 can be changed according to the formation method and the constituent material. For example, when conductive layer 3 is formed by sputtering, the thickness of conductive layer 3 is preferably 0.1 to 20 nm, and more preferably 1 to 10 nm. When conductive layer 3 is formed by printing techniques, the thickness of conductive layer 3 is preferably 0.1 to 50 μm, and more preferably 1 to 30 μm.

(2-4) Reagent Layer

As illustrated in FIG. 1, reagent layer 4 is disposed so as to be in contact with electrodes 31 to 33. Reagent layer 4 functions as the active site of sensor 1 together with electrodes 31 and 32. The "active site" is the region that is electrochemically active and that reacts with a particular substance in the liquid sample to generate an electrical signal. More specifically, reagent layer 4 contains an enzyme and an electron acceptor.

It is only necessary for reagent layer 4 to be disposed so as to come into contact with at least part of electrodes 31 and 32 (i.e., first and second electrodes). Also, reagent layer 4 may be disposed so as to come into contact further with electrode 33.

Reagent layer 4 contains an electron acceptor, a heterocyclic compound, and an enzyme. More specifically, reagent layer 4 may contain the reagent composition of the claimed invention.

The electron acceptor content in reagent layer 4 can be set to a level allowing the sensor to function, and is preferably on the order of 1 to 500 nmol, and more preferably on the order of 10 to 200 nmol, per measurement or per sensor.

The enzyme content in reagent layer 4 is set to a level allowing the detection of the target substance, and is preferably on the order of 0.2 to 20 U (units), and more preferably on the order of 0.5 to 10 U, per measurement or per sensor.

The amounts of the electron acceptor and heterocyclic compound per unit of enzyme are preferably at levels comparable to those of the components in the reagent composition.

In the present embodiment, the electron acceptor is contained in reagent layer 4; alternatively, the electron acceptor may be contained in the electrode. The electron acceptor to be contained in the electrode can be the aforementioned compounds exemplified as the electron acceptors that may be contained in the reagent composition.

The following describes the work of an electron acceptor when reagent layer 4 contains an enzyme that oxidizes a substrate. Upon oxidizing the substrate, the enzyme receives an electron from the substrate, and donates the electron to the coenzyme. As a result, the coenzyme is converted from the oxidized form to the reduced form. The oxidized form of the electron acceptor receives an electron from the reduced form of the coenzyme allowing the coenzyme to be converted back to the oxidized form. As a result, the electron acceptor itself is converted into the reduced form. The reduced form of the electron acceptor donates the electron to electrode 31 or 32 and is converted into the oxidized form. In this manner, the electron acceptor mediates electron transfer between the enzyme and the electrodes.

The coenzyme may be supported on the enzyme protein (enzyme molecule) by bonding to the enzyme protein. Alternatively, the coenzyme may be separated from the enzyme protein.

Reagent layer 4 can be formed by various methods. Examples thereof include printing and coating techniques.

A specific method of forming reagent layer 4 involves applying dropwise a predetermined amount of the aforementioned reagent composition in liquid form onto electrodes 31 and 32 using a microsyringe or the like and allowing the solution to stand in a suitable environment to dry. The aqueous solution may also be applied onto electrode 33 where necessary. The amount in which the aqueous solution is added is not limited to any specific numerical value, but is preferably 0.1 to 20 μL, and more preferably 0.5 to 5 μL.

Reagent layer 4 is not limited to any specific shape. The shape of reagent layer 4 may be rectangular, circular or the like. The surface area of reagent layer 4 (i.e., the surface area in the planar direction of substrate 2) is determined according to the size and characteristics of the device. This area is preferably 1 to 25 mm$^2$, and more preferably 2 to 10 mm$^2$.

The amounts of the enzyme, electron acceptor and other components contained in the aqueous solution to be applied are selected according to the required size and characteristics of the device.

(2-5) Spacer 5 and Capillary 51

As illustrated in FIG. 1, spacer 5 is a member to provide a gap between cover 6 and conductive layer 3 arranged on substrate 2.

More specifically, spacer 5 is a plate-shaped member that entirely covers conductive layer 3 except capillary 51 portion (described later) and the lead portion of electrodes 31 to 33. Spacer 5 has a rectangular cut-out that exposes the opposite end, from the lead portion, of electrodes 31 to 33. As spacer 5 has this cut-out, capillary 51 is constituted which is surrounded by spacer 5, conductive layer 3, and cover 6. Thus, spacer 5 provides the side walls of capillary 51 and also can define the length, width, height, etc., of capillary 51.

The volume of capillary 51 is set on the order of 0.05 to 5.0 μL (microliter), and is preferably set on the order of 0.1 to 1.0 μL (microliter). The thickness of spacer 5 is on the order of 0.02 to 0.5 mm, and is preferably set on the order of 0.1 to 0.2 mm. The length of the cut-out in spacer 5 is preferably 1 to 5 mm. The width of spacer 5 is on the order of 0.25 to 4 mm, and is preferably on the order of 0.5 to 2 mm. These dimensions may be suitably selected so that capillary 51 has the desired volume. For example, when spacer 5 has a thickness of 0.145 mm and has a cut-out with a length of 3.4 mm and a width of 1.2 mm, capillary 51 is provided that has a length of 3.4 mm, a width of 1.2 mm, a height of 0.145 mm, and volume of 0.6 μL.

Capillary 51 is an example of a sample chamber. Capillary 51 draws in the liquid sample by capillary action through inlet 52 as an opening of capillary 51, and allows the sample to be introduced on electrodes 31 to 33.

(2-6) Cover

As illustrated in FIG. 1, cover 6 is a plate-shaped member that entirely covers spacer 5. Cover 6 has a through hole that runs from the front to the back. This hole functions as vent hole 61 that extends from capillary 51 to the outside of the sensor. Vent hole 61 is an exhaust hole for discharging air inside capillary 51 to the outside of the capillary when a liquid sample is drawn into capillary 51. Discharging air in this manner makes it easier for the liquid sample to be drawn into capillary 51.

Vent hole 61 is preferably provided at a position remote from inlet 52, i.e., at the back of capillary 51 as seen from inlet 52. Disposing inlet 52 at this position allows the liquid sample to move quickly from inlet 52 to the back of capillary 51.

Further, vent hole 61 is preferably disposed more remote from inlet 52 than reagent layer 4 placed on the conductive layer of sensor 1.

<3. Sensor System>

A sensor system of the claimed invention includes the aforementioned sensor of the claimed invention, a measurement section that measures a value of current between the at least pair of electrodes, and a calculation section that measures a concentration of a target substance in the liquid sample based on the measurement result obtained from the measurement section. The sensor system of the claimed invention can be configured similarly to any of the sensor systems known in the art that electrochemically detect target substances in liquid samples. The sensor system of the claimed invention will now be described using an exemplary sensor system that includes aforementioned sensor 1.

Figure 2:
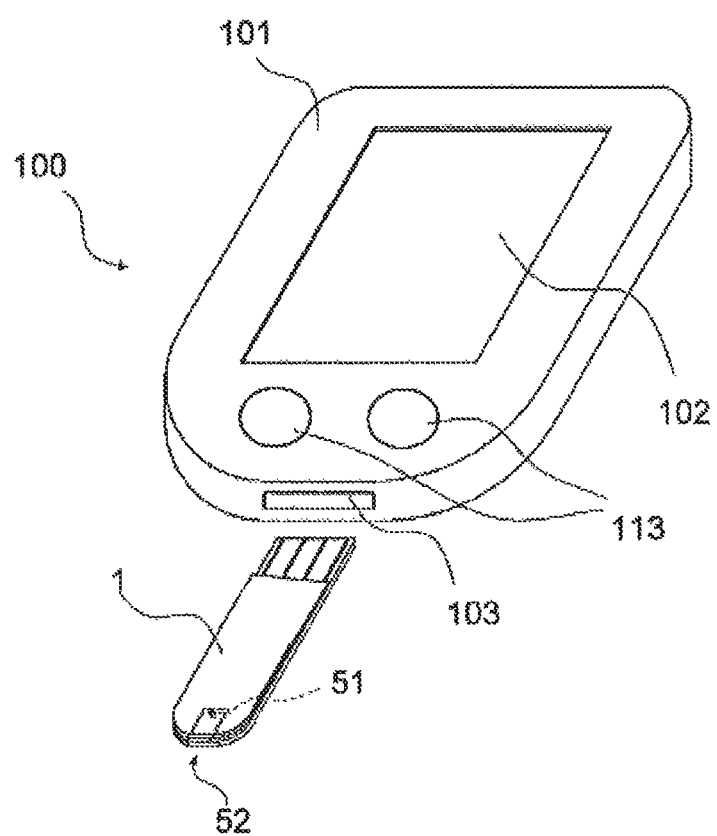
FIG. 2 is a perspective view illustrating a schematic configuration of a sensor system.

Sensor 1 is used in sensor system 100 illustrated in FIG. 2. Sensor system 100 has sensor 1 and measurement device 101.

Figure 3:
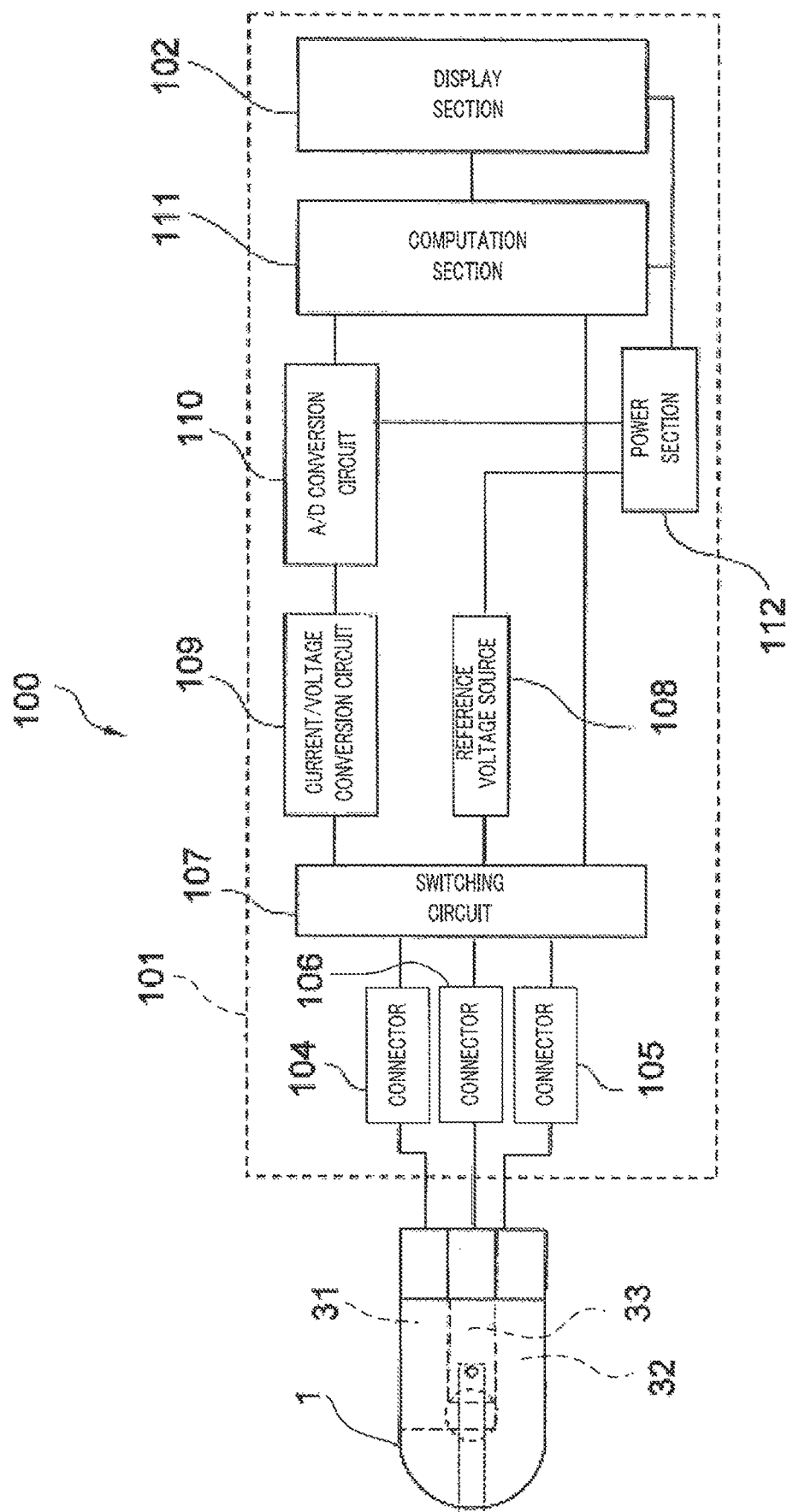
FIG. 3 is a block diagram illustrating a schematic configuration of the sensor system.

As illustrated in FIGS. 2 and 3, measurement device 101 includes display section 102, mounting section 103, switching circuit 107, reference voltage source 108, current/voltage conversion circuit 109, A/D conversion circuit 110, computation section 111, operation section 113, and power section 112. Measurement device 101 corresponds to the aforementioned measurement section. Measurement device 101 includes connectors corresponding to the respective electrodes of sensor 1. Connectors 104 to 106 provided in mounting section 103 are depicted in FIG. 3.

Display section 102 displays thereon the status of measurement device 101, measurement results, operational contents, and/or the like. Display section 102 is realized more specifically by a liquid crystal display panel.

As illustrated in FIG. 2, sensor 1 is detachably inserted into mounting section 103. As illustrated in FIG. 3, connectors 104 to 106 are respectively connected to electrodes 31 to 33 of sensor 1 when mounting sensor 1 is inserted in mounting section 103.

Switching circuit 107 can connect connectors 104 to 106 with reference voltage source 108 or with current/voltage conversion circuit 109. Reference voltage source 108 applies a voltage to electrodes 31 to 33 via connectors 104 to 106.

Current/voltage conversion circuit 109 receives a current from sensor 1 via connectors 104 to 106, converts the current into voltage, and outputs the voltage to A/D conversion circuit 110. A/D conversion circuit 110 converts the voltage value (analog value), an output from current/voltage conversion circuit 109, into a digital value.

Computation section 111 includes a central processing unit (CPU), as well as a recording medium such as read only memory (ROM) and random access memory (RAM). Computation section 111 calculates the concentration of a target substance, and controls the operation of the respective sections in measurement device 101. Computation section 111 corresponds to the aforementioned calculation section.

The concentration calculation function of computation section 111 will now be described. The recording medium in computation section 111 stores therein a conversion table used for determining the concentration of the target substance in the sample; a correction amount table used for determining the correction amount of the concentration; and so forth. Computation section 111 refers to this conversion table and calculates a tentative concentration of the target substance based on a pulse from A/D conversion circuit 110. Computation section 111 uses the correction amount in the correction amount table to determine the final concentration of the target substance. The concentration thus calculated is displayed on display section 102.

Computation section 111 has, in addition to the concentration calculation function, such functions as controlling the switching of switching circuit 107, controlling the voltage of reference voltage source 108, measuring time upon concentration measurement and correction amount selection (i.e., timer function), outputting display data to display section 102, and communicating with external devices. The various functions of computation section 111 are realized by allowing the CPU to read and execute the programs stored in the ROM and/or the like (not illustrated).

Operation section 113 is provided on the surface of measurement device 101. Operation section 113 is composed of operation buttons and/or the like which the user use when, for example, referring to the measurement data and/or setting data.

Power section 112 is composed of a battery and/or the like which supplies power to the aforementioned electric circuits, display section, computation section, and/or the like.

<4. Use of Sensor System>

The sensor system of the claimed invention is advantageously used in the method of measuring the concentration of a target substance. The concentration measurement method includes: (a) bringing a reagent composition containing at least an electron acceptor and an enzyme into contact with a liquid sample; (b) detecting the current generated in the step (a); and (c) measuring the concentration of a target substance in the liquid sample based on the detection result obtained in the step (b). As this reagent composition, the aforementioned reagent composition of the claimed invention is used.

The concentration measurement method of the claimed invention employs the aforementioned reagent composition as the material of a reagent layer, and therefore includes such a reagent layer that does not cause the aforementioned enzyme deactivation due to moisture absorption by the reagent layer. Thus, the concentration measurement method of the claimed invention allows for the measurement of concentrations of target substances with higher accuracy.

The concentration measurement by sensor system 100 will now be described.

When sensor 1 is inserted into mounting section 103, connectors 104 to 106 are connected to electrodes 31 to 33, respectively. Also, a switch (not illustrated) inside mounting section 103 is pressed by the insertion of sensor 1 into mounting section 103. The switch is pressed and turned on, and computation section 111 determines that sensor 1 has been mounted and puts measurement device 101 in a condition ready for sample loading. The condition ready for sample loading refers to a state of measurement device 101 where voltage application by reference voltage source 108 between working electrode 31 and sensing electrode 33 via connectors 104 and 106 and the measurement of a current by current/voltage conversion circuit 109 have both started under the control of computation section 111, but the liquid sample has yet to be supplied for measurement.

When the user provides a droplet of a liquid sample in inlet 52 of sensor 1, the liquid sample is drawn in through inlet 52 into capillary 51 by capillary action. As the liquid sample, biological liquid samples such as blood, perspiration, and urine; environmental liquid samples; food-derived liquid samples; and so forth can be used. For example, when sensor 1 is used as a blood glucose sensor, the user pricks his/her finger, palm, arm or other body part and squeezes out a small amount of blood for use as a liquid sample to be measured in sensor 1.

When the liquid sample reaches working electrode 31 and sensing electrode 33, there is a change in the current value to be received by computation section 111 via current/voltage conversion circuit 109. Computation section 111 determines, based this current change, that the liquid sample has been drawn into sensor 1 without any trouble. Measurement starts when the drawing of the liquid sample is detected in this manner.

Inside sensor 1, an enzyme, an electron acceptor and other components in reagent layer 4 dissolve in the liquid sample. This brings the liquid sample, enzyme and electron acceptor into contact with one another on electrodes 31 and 32 of sensor 1.

Control by computation section 111 causes switching circuit 107 to connect connectors 104 and 105 to reference voltage source 108 and current/voltage conversion circuit 109. A voltage is thereby applied between working electrode 31 an counter electrode 32, and the current generated between working electrode 31 and counter electrode 32 is transmitted to current/voltage conversion circuit 109.

The current flowed to current/voltage conversion circuit 109 is converted into voltage. This voltage is converted into a digital value by A/D conversion circuit 110. Computation section 111 calculates the concentration of a specific component based on the digital value. The value calculated by the computation section 111 is displayed on display section 102. Other information can also be displayed for the user at the same time.

Upon completion of the measurement, the user can detach sensor 1 from mounting section 103.

Reference voltage source 108 is designed to apply a voltage enough to induce the desired electrochemical reaction between the two electrodes 31 and 32. This voltage is set mainly according to the chemical reaction and electrodes being used.

As is clear from the aforementioned description, when sensor system 100 is used, a concentration measurement method is executed that includes: (a) bringing a liquid sample, an electron acceptor, and an enzyme into contact with one another; (b) detecting a current generated by the step (a); and (c) measuring the concentration of a target substance based on the detection result obtained in the step (b).

When a liquid sample such as blood is used, measurement system 100 executes a concentration measurement method that includes: (i) dissolving in the liquid sample an electron acceptor and an enzyme whose substrate is the target substance and which donates an electron to the electron acceptor; (ii) detecting the current generated in the solution obtained in the step (i); and (iii) calculating the concentration of the target substance based on the detection result obtained in step (ii).

[Advantages of Quinone Compound Having a Hydrophilic Functional Group]

A quinone compound having a hydrophilic functional group is suitable particularly where the reagent composition is applied to a sensor designed for measurements for aqueous samples (e.g., blood). When the electron acceptor is a quinone compound having a hydrophilic functional group, the chances of contacting molecules of the electron acceptor with enzyme molecules in the sample increase. As a result, the reaction rate increases, so that there may be an increase in the amount of a current derived from the target substance, and the measurement time may be shortened as well.

When the electron acceptor is a quinone compound having a hydrophilic functional group, there is no need to formulate fillers or binders, which are necessary for immobilizing the electron acceptor, in or on the working electrode. Specifically, when the electron acceptor functions by dissolving into the sample, the electron acceptor can be easily disposed on the electrode by applying dropwise an electron acceptor-containing solution onto the electrode and drying the solution, as described above.

The electron acceptor is preferably disposed so as to be in contact with at least part of the pair of the electrodes constituting the sensor, i.e., at least part of the first electrode and at least part of the second electrode. The first and second electrodes correspond to the working electrode and counter electrode, respectively. By disposing the electron acceptor in this manner, the potential of each electrode is stabilized, whereby measurement accuracy improves. Because the measurement is carried out as an electrochemical reaction proceeds by the application of a voltage between the first and second electrodes, when the electron acceptor is in contact with part of the two electrodes, a stable reduction potential of the electron acceptor is imparted to the counter electrode, as a result of the reduction reaction of the electron acceptor at the electrode. On the other hand, the potential of the working electrode becomes stable as it equals the applied voltage plus the reduction potential of the electron acceptor.

From the perspective of the long-term stability, etc. of the sensor, a quinone free from any attached hydrophilic functional group is preferably contained in the electrodes. Specifically, the electrodes are preferably formed from a mixture of a quinone and a conductive material. A method is known in which fillers or binders are formulated in or on the working electrode so that electron acceptor molecules are immobilized.

[Preferable Range of Redox Potential of Electron Acceptor and Advantages Thereof]

Upon detection of a target substance by sensor 1, there are cases where the sample contains an inhibitory substance, which impedes accurate detection of the target substance by sensor 1. Such an inhibitory substance may also be referred to as an interfering substance. Examples of the interfering substance include ascorbic acid, uric acid, and acetaminophen. When the measurement target is a non-biological sample (i.e., sample other than blood, urine or other such biological sample), the inhibitory substance is a readily oxidizable substance contained in the non-biological sample.

As discussed above, when the potential required to oxidize an inhibitory substance is lower than the potential required to oxidize the electron acceptor, the inhibitory substance impacts the measurement results of the sensor, resulting in measurement errors. For example, when the sample is blood, measurement errors occur where the electrode potential required to oxidize the electron acceptor is significantly higher (more positive) than the electrode potential that is required to oxidize ascorbic acid or other inhibitory substance contained in the blood.

The electrode potential required to oxidize the electron acceptor depends on the redox potential of the electron acceptor itself. Thus, it is preferable, in terms of reducing the impact of inhibitory substances, for the redox potential of the electron acceptor to be more negative. Even when the redox potential of the electron acceptor is more positive than the oxidation potential of the inhibitory substances, the impact of the inhibitory substances can be lessened by using an electron acceptor having a redox potential as close as possible to that oxidation potential. To further lessen this impact, it is preferable to use an electron acceptor having a redox potential that is more negative than the oxidation potential of the inhibitory substances.

When the enzyme oxidizes the target substance, the redox potential of the electron acceptor is preferably more positive than that of the coenzyme. This allows the electron acceptor to easily accept electrons from the coenzyme.

When the enzyme reduces the target substance, the redox potential of the electron acceptor is preferably more negative than that of the coenzyme. This allows the electron acceptor to easily donate electrons to the coenzyme. When the target substance is detected by a reduction reaction as described above, the relation among the potentials of the coenzyme, the electron acceptor, and the inhibitory substances (i.e., readily oxidizable substances) becomes the opposite from that when the target substance is detected by oxidation.

The following describes a case in which a target substance is detected by oxidation The specific redox potentials of coenzymes are as follows. Coenzyme FAD and PQQ typically function in cooperation with an enzyme protein while being bound to the enzyme protein. The redox potential of these coenzymes is approximately −300 mV and approximately −200 mV, respectively. NAD functions without binding to an enzyme protein. The redox potential of NAD is approximately −520 mV.

The ability of an electron acceptor to accept electrons tends increase as the redox potential of the electron acceptor is more positive with respect to the that of the coenzyme.

Specifically, the greater is the difference in redox potential between the electron acceptor and coenzyme, the greater is the difference in energy level. Thus, the electron acceptor accepts electrons faster. Therefore, in terms of increasing the measurement sensitivity and measurement speed of a sensor, it is preferable for the redox potential of the electron acceptor to be high at positive values.

In order to realize a sensor and measurement method with good sensitivity and less measurement errors, as discussed above, the positive values range of the redox potential of the electron acceptor are limited by the redox potential of the interfering substances, and the negative values range are limited by the redox potential of the coenzyme, which are related to the ability to accept electrons. This range is sometimes extremely narrow.

For example, Patent Literature 2 discloses a sensor having an NAD-dependent enzyme as well as phenanthroline quinone as an electron acceptor, which is a nitrogen-containing heterocyclic compound. The redox potential of phenanthroline quinone is approximately 0 mV, and the redox potential of NAD is approximately −520 mV. Thus, there is a potential difference of approximately 520 mV between the electron acceptor and the coenzyme. Because the oxidation potential of ascorbic acid is approximately −140 mV, when the electron acceptor is phenanthroline quinone, the impact of interfering substances cannot be completely avoided for the reasons mentioned above.

As discussed above, a sensor having a PQQ-dependent or FAD-dependent enzyme has the advantage of being able to be manufactured at low cost. However, since PQQ and FAD have a higher redox potential than NAD, the number of kinds of electron acceptor with enough low redox potential to be applied to the PQQ-dependent and FAD-dependent enzymes is not large. At present, there is a need for an electron acceptor with enough low redox potential to be applied to PQQ-dependent and FAD-dependent enzymes, in order to lessen the impact of interfering substances and to keep manufacturing costs low.

However, when the coenzyme is FAD or PQQ, since the potentials of these coenzymes are more positive, the aforementioned range is particularly narrow. The redox potentials of 9,10-phenanthrenequinone, 9,10-phenanthrenequinone-2-sulfonic acid, 1,2-naphthoquinone-4-sulfonic acid, and 2,5-dimethyl-1,4-benzoquinone, which are exemplary electron acceptors, are −180 mV, −140 mV, −16 mV, and −5 mV, respectively. These redox potentials are more negative than 0 mV, more positive than the potential of NAD, and more positive than the potential of FAD and PQQ. In particular, the redox potentials of 9,10-phenanthrenequinone and 9,10-phenanthrenequinone-2-sulfonic acid are more negative than the oxidation potential of ascorbic acid (approximately −140 mV). Specifically, these electron acceptors are applicable to sensors having a PQQ-dependent or FAD-dependent enzyme. Also, these electron acceptors can lessen the impact of inhibitory substances on the detection results.

It should be noted that the ability to accept electrons from the coenzyme is determined not solely by the potential relation. The ability of a quinone compound to accept electrons is also affected by the relation between the electrical charge of the quinone compound and the charge near the active site of the enzyme; the relation between the size of the quinone compound molecules and the size of the active site space of the enzyme; and so forth.

When the enzyme is an FAD-dependent or PQQ-dependent enzyme, the electron acceptor is preferably 9,10-phenanthrenequinone (including its derivative). 9,10-Phenanthrenequinone has a compact molecular size as the aromatic rings are not linked side by side like anthraquinone. Thus, it is deduced that 9,10-phenanthrenequinone can readily work its way into the active site space of the enzyme. Also, since 9,10-phenanthrenequinone does not have any electrical charge, it is predicted that 9,10-phenanthrenequinone is less likely to be affected by the charge at the active site of the enzyme.

EXAMPLES

[1] Limitation of Changes in Oxidization Potentials of Electron Acceptors by Heterocyclic Compounds As will be demonstrated hereinafter, heterocyclic compounds offer the effects of limiting changes in the oxidation potentials of electron acceptors between before and after the storage period, and of shifting of the redox potentials of electron acceptors to negative potentials. The following particularly provides experimental results for quinone compounds employed as an electron acceptor.

[1-1] Preparation of Sodium 9,10-Phenanthrenequinone-2-Sulfonate (PQSA)

Sodium 9,10-phenanthrenequinone-2-sulfonate (PQSA) represented by the following formula (i) was prepared in the procedure described below.

[Formula 6]

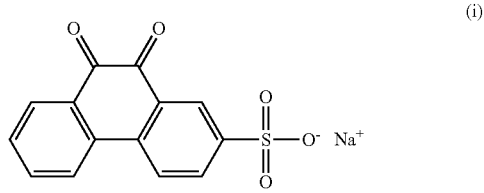

A commercially available 9,10-phenanthrenequinone was sulfonylated with fuming sulfuric acid, isomers were isolated, and the sulfonylated 9,10-phenanthrenequinone was converted into sodium salt to afford PQSA, a compound of interest. The reaction scheme is as follows.

[Formula 7]

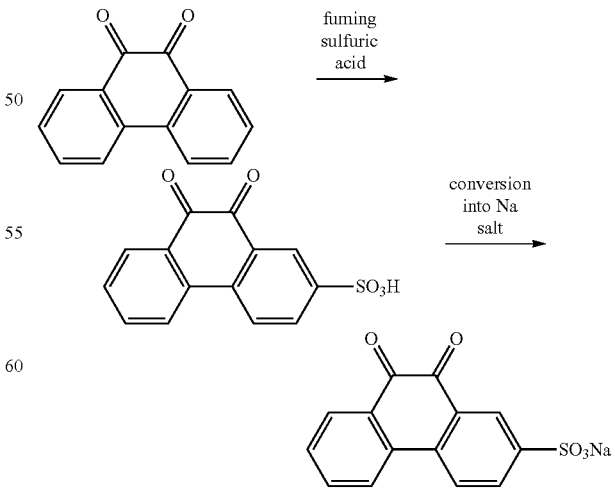

PQASA showed a solubility in water of as high as 80 mM.

[1-2] Preparation of Reagent Compositions (Reagent Solutions)

Reagent solutions A and B having the following compositions were prepared.

<Reagent Solution A>

Additive: Imidazole (structural formula is illustrated below) (7.5 mM)

Electron acceptor: PQSA (7.5 mM)

Enzyme: FAD dependent-glucose dehydrogenase (FAD-GDH) 3.5 MU/L (liter)

Buffer solution: 100 mM sodium phosphate buffer solution (pH 7.0)

[Formula 8]

<Reagent Solution B>

Reagent solution B has the same composition as reagent solution A except the absence of imidazole.

[1-3] Manufacture of Sensor Electrode

A sensor electrode for characterizing reagent solutions A and B was manufactured. This electrode has the same configuration as that illustrated in FIG. 1 except the absence of reagent layer 4. The detailed procedure will now be described.

First, by sputtering palladium, 8 nm-thick conductive layer 3 was deposited on substrate 2 which was 30 mm in length, 7 mm in width and 0.2 mm in thickness and which contained polyethylene terephthalate as its main component. Thereafter, a 0.1 mm-width non-conductive track was formed by laser ablation, to form electrodes 31 to 33. Electrode 31 corresponds to a working electrode, and electrode 32 to a counter electrode. Spacer 5 (0.145 mm thick) having a cut-out with a length of 3.4 mm and a width of 1.2 mm and cover 6 were sequentially attached to the substrate having the electrodes formed thereon. In this way a sensor electrode was manufactured that has capillary 51 with a volume of 0.6 µL.

[1-4] Cyclic Voltammetry

Cyclic voltammetry was performed for the resultant reagent solution using the aforementioned sensor electrode. As a reference electrode, a silver/silver chloride (saturated potassium chloride) electrode (hereinafter "Ag|AgCl") was used. The reference electrode was led to vent hole 61 of the sensor electrode via a salt bridge. A potentiostat was used for measurement. The electrodes and the potentiostat used were those commonly used in electrochemistry. These instruments can be purchased from BAS Inc., for example.

In cyclic voltammetry, a potential applied to the working electrode was swept linearly with respect to time. The sweeping rate was set to 0.1 V/second. First, a first potential was applied to the working electrode, and the electrode potential was swept toward negative potentials from the first potential to a second potential. The electrode potential was then swept back from the second potential to the first potential toward positive potentials. The first and second potentials were 0.2 V and 0.5 V, respectively, When the electrode potential is swept to positive potentials in the cyclic voltammetry, the relation between the oxidation potential and oxidation current for fresh (initial) reagent solution A is indicated by dotted line in FIG. 4, and the same for reagent solution A after 21 hours (i.e., reagent solution A stored at 25° C. and 5% relative humidity for 21 hours) is indicated by solid line in FIG. 4. Similarly, the result of cyclic voltammetry for fresh reagent solution B is indicated by dotted line in FIG. 5, and the same for reagent solution B after 21 hours (i.e., reagent solution B stored at 25° C. and 5% relative humidity for 21 hours) is indicated by solid line in FIG. 5.

[1-5] Manufacture of Sensor

A sensor having the configuration illustrated in FIG. 1 was manufactured. The detailed procedure will now be described. First, by sputtering palladium, 8 nm-thick conductive layer 3 was deposited on substrate 2 which was 30 mm in length, 7 mm in width and 0.2 mm in thickness and which contained polyethylene terephthalate as its main component. Thereafter, a 0.1 mm-width non-conductive track was formed by laser ablation, to form electrodes 31 to 33. Electrode 31 was designed to function as a working electrode, electrode 32 as a counter electrode, and electrode 33 as a sensing electrode.

Reagent solutions C and D having the following compositions were prepared.

<Reagent Solution C>

Additive: Imidazole: 7.5 mM

Enzyme: FAD-GDH 4 U/sensor

Electron acceptor: PQSA 0.46 wt % (15 mM)

Polymer: Carboxymethyl cellulose (0.25 wt %)

Buffer solution: Phosphate buffer (concentration: 0.2 wt %, pH 6.5)

| | |
|---|---|
| $NaH_2PO_4$ | 0.11 wt % (9 mM) |
| $KH_2PO_4$ | 0.04 t % (3 mM) |
| $K_2HPO_4$ | 0.05 wt % (3 mM) |

<Reagent Solution D>

Reagent solution D has the same composition as reagent solution C except the absence of imidazole.

Using a microsyringe, 1.2 µL of each reagent solution was applied to form reagent layer 4 in a shape of 2.2 mm diameter-circular. After formation of reagent layer 4, spacer 5 (0.145 mm thick) having a cut-out with a length of 3.4 mm a width of 1.2 mm and cover 6 were sequentially attached to the substrate having the electrodes formed thereon. In this way a sensor was manufactured that has a capillary having a volume of 0.6 µL.

For each of reagent solutions C and D described below, two different sensors were manufactured, one using the fresh reagent solution, and the other using the reagent solution stored at 25° C. and 5% humidity for 21 hours after preparation.

[1-6] Measurement of Response Current Value

Figure 6:
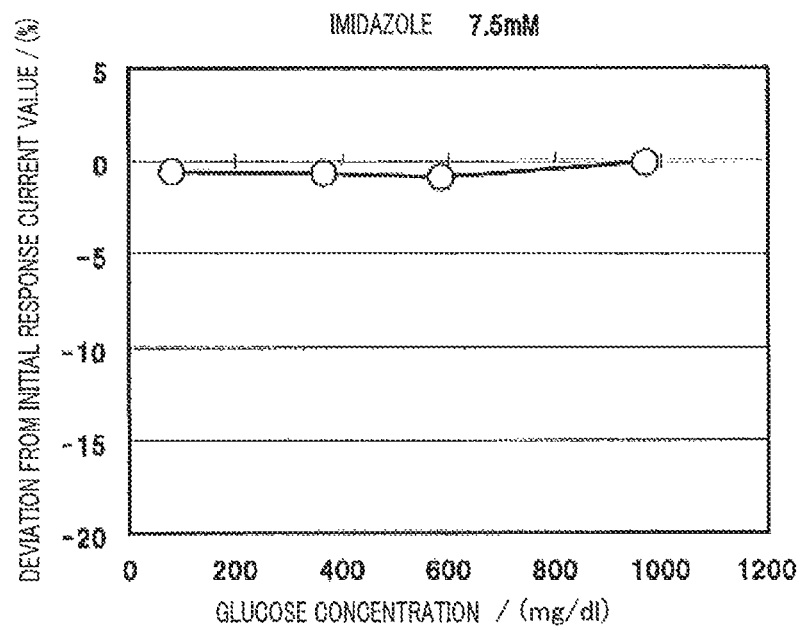
FIG. 6 is a graph showing a deviation of a response current value of a sensor manufactured using an imidazole-containing reagent solution stored for 21 hours after its preparation, from a response current value of a sensor manufactured using the same reagent solution immediately after preparation (i.e. an initial response current value)
Figure 7:
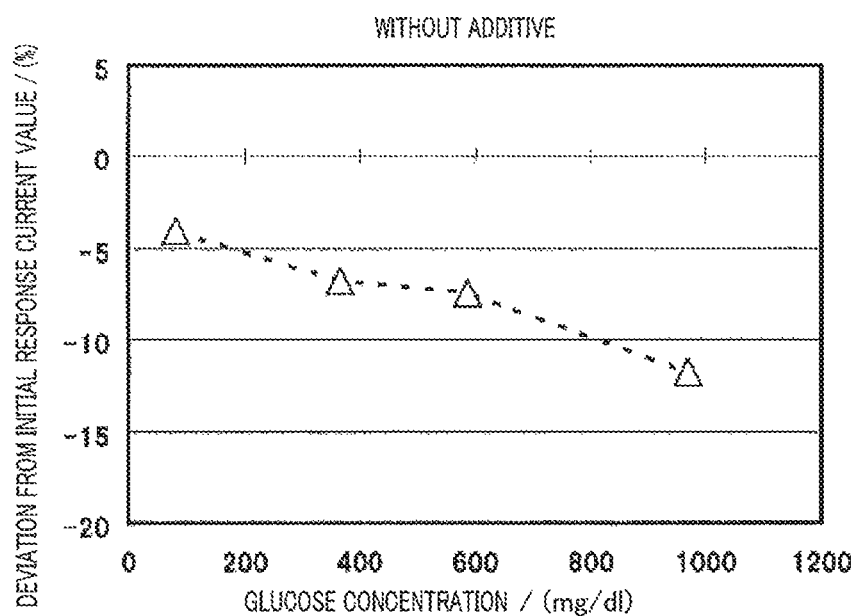
FIG. 7 is a graph showing a deviation of a response current value of a sensor manufactured using an imidazole-free reagent solution stored for 21 hours after its preparation, from a response current value of a sensor manufactured using the same reagent solution immediately after preparation (i.e., an initial response current value)

Response current values of each sensor were measured using a series of glucose solutions of known concentrations. FIG. 6 shows a deviation of a response current value of the sensor manufactured using reagent solution C after 21 hours storage, from a response current value of the sensor manufactured using fresh reagent solution C. FIG. 7 shows a deviation of a response current value of the sensor manufactured using reagent solution D after 21 hours storage, from a response current value of the sensor manufactured using fresh reagent solution D. The deviation is expressed as percent change in the response current value of the sensor manufactured using the reagent solution after 21 hours storage, with respect to a response current value of the sensor manufactured using the fresh reagent solution.

[1-7] Results

[Cyclic Voltammetry]

Figure 5:
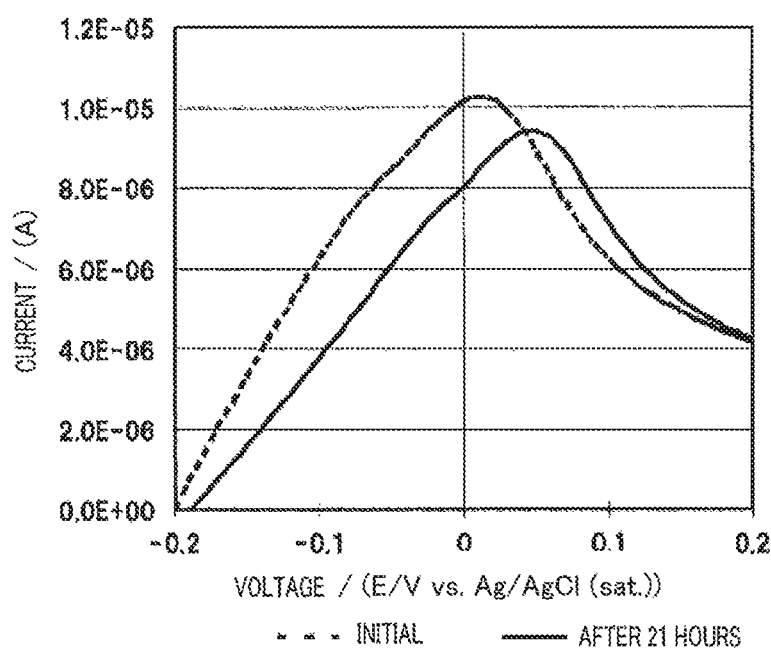
FIG. 5 is cyclic voltammograms for a fresh (initial) imidazole-free, PQSA-containing reagent solution (dotted line), and for the same reagent solution 21 hours after its preparation (solid line)

As shown in FIG. 5, for reagent solution B (free from imidazole), the oxidation potential of PQSA shifted to positive potentials 21 hours after the initial measurement. Such a potential change is considered to be due to the coexistence of an electron acceptor and an enzyme in aqueous solution.

Figure 4:
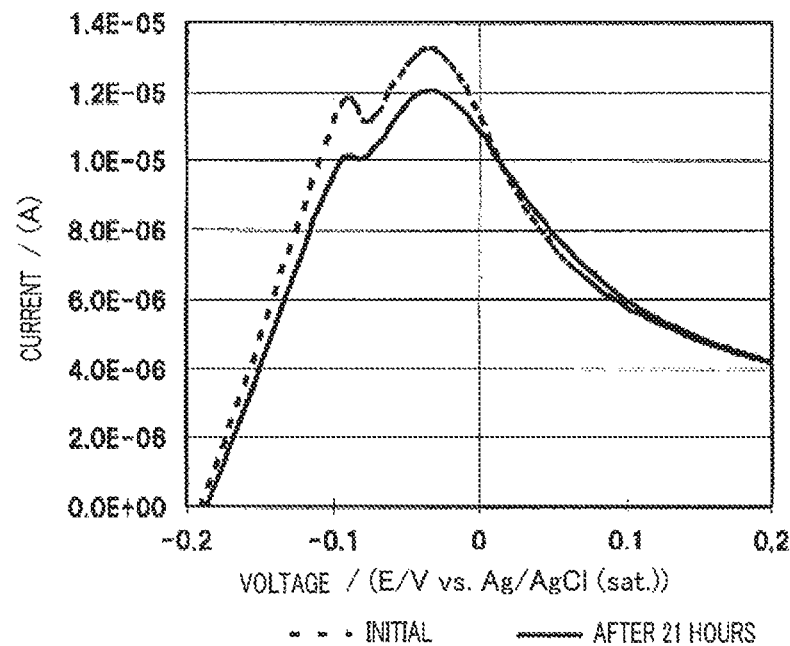
FIG. 4 is cyclic voltammograms for a fresh (initial) reagent solution containing imidazole and sodium 9,10-phenanthrenequinone-2-sulfonate (PQSA) (dotted line), and for the same reagent solution 21 hours after its preparation (solid line)

Comparison between FIGS. 4 and 5 reveals that addition of imidazole (7.5 mM) as the heterocyclic compound in the reagent solution caused the negative shift of the peak potential of PQSA. Comparison between the dotted line and solid line in FIG. 4 also reveals that the positive shift of the peak oxidation potential was limited. The inventors confirmed that similar effects were obtained for other heterocyclic compounds.

[Response Current Value of Sensor]

Comparison between FIGS. 6 and 7 reveals that the addition of the heterocyclic compound in the reagent solution limited the deviation of the response current value, measured after 21 hours storage, from the initial response current value, in comparison to cases where no heterocylic compound is added in the reagent solution.

[2] Experiments using Various Heterocylic Compounds

[2-1] Preparation of Reagent Solutions

By adding as an additive imidazole, histamine, histidine, 2-aminoimidazole, 4,5-bis(hydroxymethyl)imidazole, 1,2,4-triazole, 3-amino-1,2,4-triazole, 4-amino-1,2,4-triazole, 3,5-diamino-1,2,4-triazole, 2-methylimidazole, or 1,2-dimethyl-imidazole, reagent solutions were prepared that contain the same composition as reagent solution C except the type and concentration of the additive. The concentrations of the additives are as indicated in Tables below and the accompanying drawings.

[Formula 9]

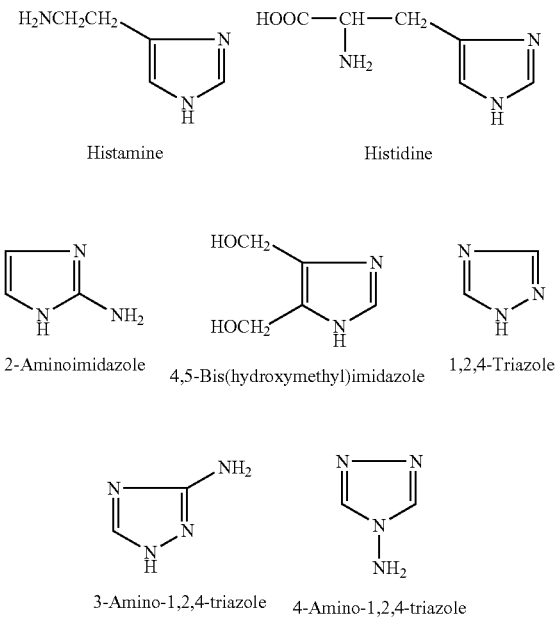

-continued

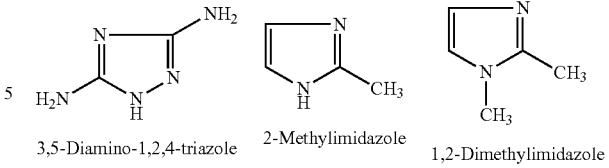

In addition, reagent solutions containing a diamine compound (ethylenediamine, butanediamine, pentanediamine, hexanediamine, ethyleneamine, ornithine, lysine, or arginine) instead of the heterocyclic compound were prepared.

[2-2] Storage Stability of Reagent Solution

Sensors were manufactured in the same manner as described in section [1-5] using the reagent solutions prepared above. Further, sensors were manufactured using the same reagent solutions stored at 25° C. and 5% humidity for 24 hours after preparation.

[2-3] Stability Test (Exposure Test) of Sensor

Sensors were manufactured in the same manner as described in section [1-5] using the reagent solutions prepared above. The sensors manufactured were exposed to an environment of high temperature and humidity (30° C., 80% relative humidity) for 24 hours. Response current values of the pre- and post-exposed sensors were measured for a series of glucose solutions of known concentrations.

[2-4] Results

As seen in Table 3, other heterocyclic compounds similarly offered the effect of preventing the positive shift of the oxidation potential of an electron acceptor, i.e., the effect of enhancing the stability of reagent solution. Some diamine compounds also offered the effect of enhancing the stability of reagent solution.

However, as seen in Table 3, the response current values for the sensors in which the diamine compound is added to the reagent layer showed a significant reduction after sensor exposure. When comparing between with and without the addition of the diamine compound except for arginine, a reduction rate of the current were large for the reagent layers containing the diamine compound.

It is deduced that such current reductions resulted from additive-induced enzyme deactivation that occurs when the dry reagent slightly dissolves by exposure to moisture. That is, the additive at a high concentration in the solution can deactivate the enzyme, although the additive at a low concentration in the solution contributes to the mediator's stability.

By contrast, as seen in Table 3, sensors that include a reagent layer containing histamine, histidine, 2-aminoimidazole, 4,5-bis(hydroxymethyl)imidazole, 1,2,4-triazole, 3-amino-1,2,4-triazole, 4-amino-1,2,4-triazole, or 3,5-diamino-1,2,4-triazole showed a relatively small change in the response current value even after the exposure test.

TABLE 3

| | Additive | Conc. (mM) | Reagent solution stability % change in response current value between before and after 24 hours storage at 25° C. | Sensor stability % change in response current value between before and after 24 hours exposure at 30° C. and 80% humidity | Initial response current value (μA) Glucose conc.: 1,000 mg/dL |
|---|---|---|---|---|---|
| | No additive | — | −34 | −15 | 17.6 |
| Diamines | Ethylenediamine | 2.0 | −3 | −45 | 21.9 |
| | Butanediamine | 2.5 | — | −51 | 19.2 |
| | Pentanediamine | 2.5 | — | −63 | 18.9 |
| | Hexanediamine | 2.5 | — | −58 | 20.5 |
| | Ethyleneamine | 2.5 | — | −77 | 11.5 |
| | Ornithine | 1.0 | −19 | −22 | 14.8 |
| | Lysine | 1.0 | −20 | −31 | 16.2 |
| | Arginine | 1.0 | −25 | −12 | 18.8 |
| Heterocyclic compuonds | Imidazole | 5.0 | −1 | −50 | 20.7 |
| | 1,2,4-Triazole | 2.5 | −12 | −14 | 20 |
| | 2-Methylimidazle | 2.5 | 1 | −44 | 15.9 |
| | 1,2-Dimethylimidazole | 2.5 | 2 | −44 | 5.9 |
| | Histidine | 1.0 | −7 | −12 | 16.7 |
| | 3-Amino-1,2,4-triazole | 1.0 | 0 | −4 | 27.3 |
| | 4-Amino-1,2,4-triazole | 1.0 | −6 | −4 | 23 |
| | 3,5-Diamino-1,2,4-triazole | 1.0 | −1 | −2 | 25.7 |
| | Histamine | 1.0 | −2 | −3 | 23.1 |
| | 2-Aminoimidazole | 1.0 | −6 | −7 | 17.9 |
| | 4,5-Bis(hydroxymethyl) imidazole | 1.0 | −14 | −11 | 19.6 |

[3] Concentration of Additive

Reagent solutions containing different concentrations (0.01 to 6 mM) of 3-amino-1,2,4-triazole were prepared. A reagent solution having the same composition except the absence of 3-amino-1,2,4-triazole was also prepared. Sensors were manufactured using the fresh reagent solutions and the same the reagent solutions stored at 25° C. and 5% humidity for 24 hours after preparation. Response current values of the sensors were measured for a series of glucose solutions of known concentrations.

Figure 8:
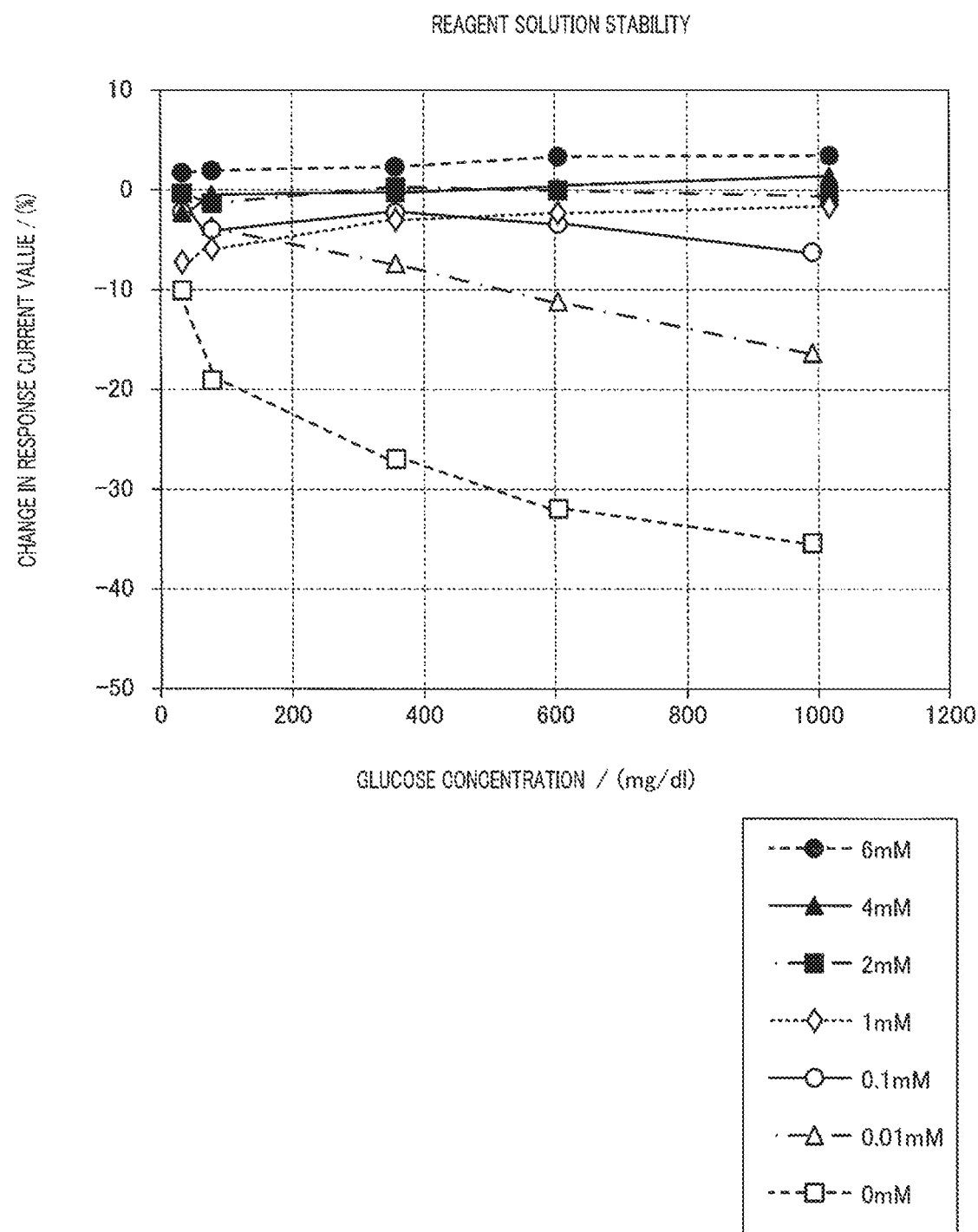
FIG. 8 is a graph showing change ratios of response current values of sensors manufactured using reagent solutions stored for 24 hours at 25° C. and 5% humidity, with respect to response current values of sensors manufactured using the same reagent solutions immediately after preparation (additive: 3-amino-1,2,4-triazole)

FIG. 8 shows changes ratios of the response current values between before and after storage. In FIG. 8, the change ratio is expressed as percent change in the response current value of the sensor after storage, with respect to a response current value of the sensor manufactured using the fresh reagent solution being 0%. As seen in FIG. 8, the addition of the heterocyclic compound offered the effect of enhancing the stability of reagent solution over the entire concentration range studied (0.01 to 6 mM). A significant effect was observed particular in the concentration range of 1 to 6 mM.

Sensors were manufactured using fresh reagent solutions having the same compositions as described above. The sensors were subjected to an exposure experiment where they were allowed to stand for 24 hours at 30° C. and 80% humidity. Response current values of non-exposed sensors (i.e., sensors stored under the ambient condition (25° C., 5% humidity) for 24 hours) and the exposed sensors were measured for a series of glucose solutions of known concentrations.

Figure 9:
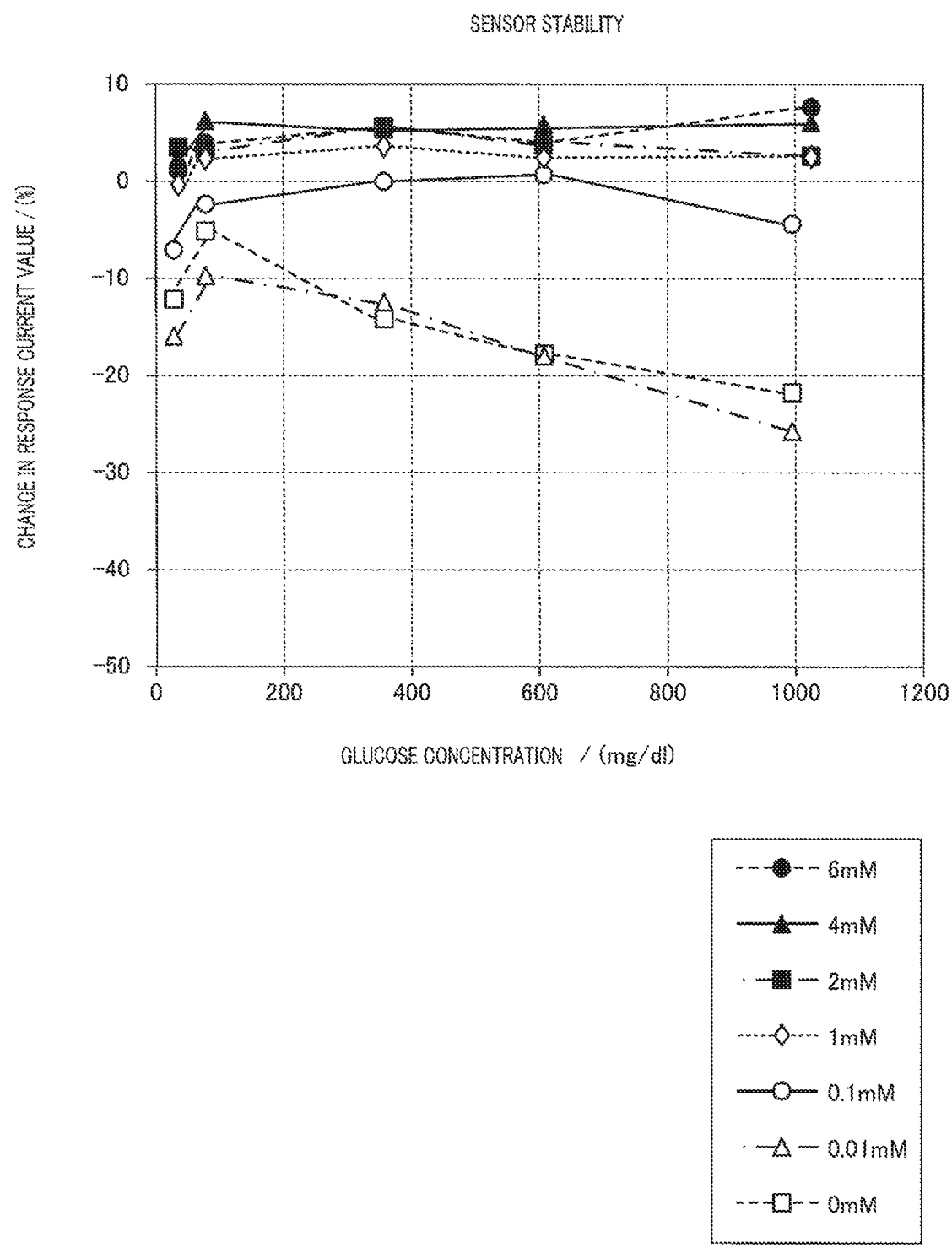
FIG. 9 is a graph showing change ratios of response current values of sensors exposed to an environment of 30° C. temperature and 80% humidity for 24 hours, with respect to response current values of sensors stored for 24 hours at 25'C and 5% humidity (additive: 3-amino-1,2,4-triazole)

FIG. 9 shows changes ratios of the response current values between before and after the exposure. In FIG. 9, the change ratio is expressed as percent change in the response current value of the sensor after the exposure, with respect to the response current value of the non-exposed sensor being 0%. As seen in FIG. 9, the effect of limiting the response current reduction due to exposure was observed particularly in the concentration range of 0.1 to 6 mM.

[4] Impacts on Redox Potential

Cyclic voltammetry was performed for reagent solutions E and F having the composition described below. The electrodes used were as follows:

Working electrode: glassy carbon electrode
Counter electrode: platinum wire
Reference electrode: Ag|AgCl <Reagent Solution E>
Additive: 3-amino-1,2,4-triazole (5 mM)
Electron acceptor: PQSA (2 mM)
Buffer solution: 100 mM sodium phosphate buffer solution (pH 7.0)

<Reagent Solution F>
Reagent solution F has the same composition as reagent solution E except that 2,6-dimethylbenzoquinone is contained as an electron acceptor.

<Reagent Solution G>
Reagent solution G has the same composition as reagent solution E except that potassium ferricyanide is contained as an electron acceptor.

Figure 10:
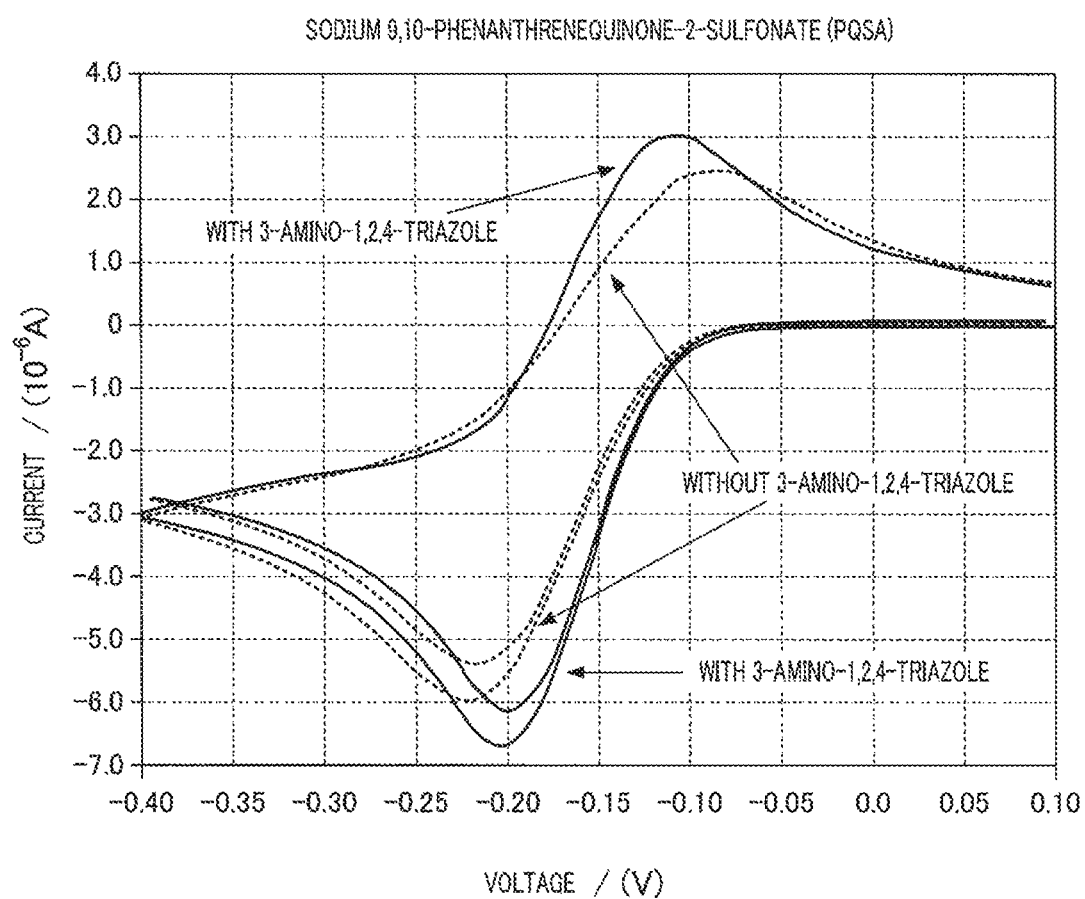
FIG. 10 is cyclic voltammograms for PQSA in the presence and absence of 3-amino-1,2,4-triazole.
Figure 11:
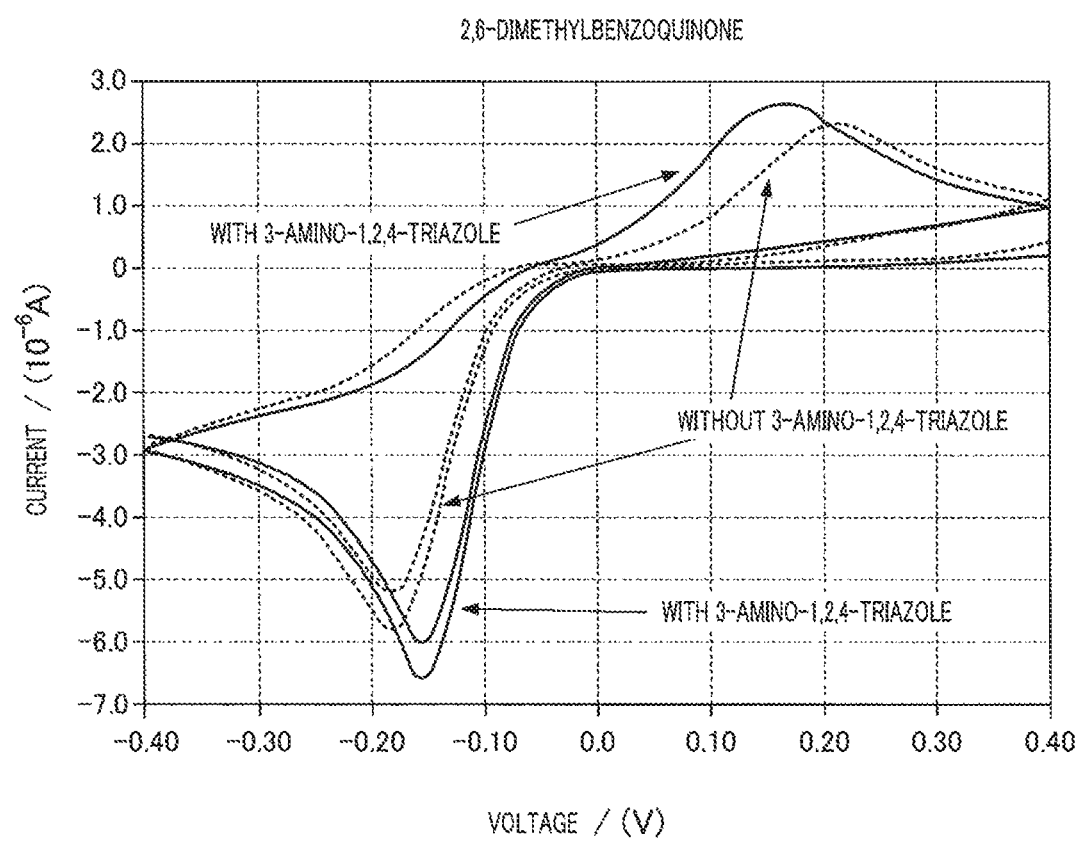
FIG. 11 is cyclic voltammograms for 2,6-dimethylbenzoquinone in the presence and absence of 3-amino-1,2,4-triazole.
Figure 12:
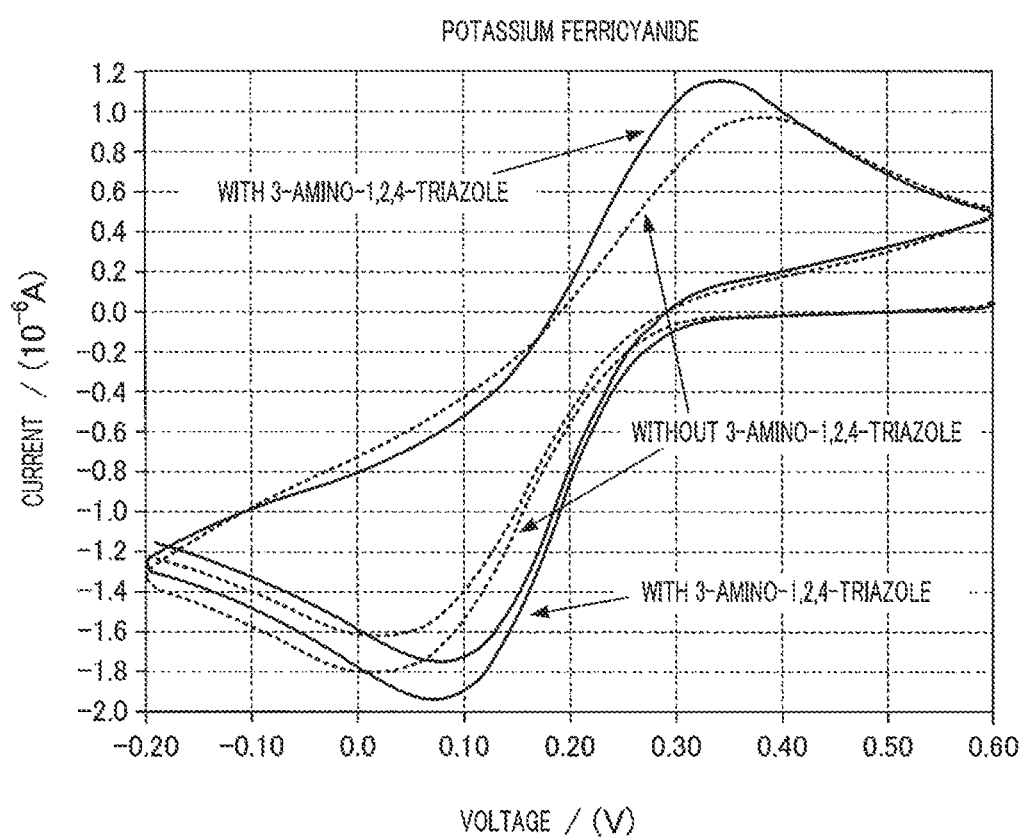
FIG. 12 is cyclic voltammograms for potassium ferricyanide in the presence and absence of 3-amino-1,2,4-triazole.

As seen in FIGS. 10 to 12, the negative shift of the oxidation potential was observed for all of reagent solutions E, F, and G.

As demonstrated above, the addition of a specific nitrogen-containing compound such as triazole to a reagent solution containing an oxidoreductase and an electron acceptor caused the oxidation potentials of the electron acceptors to be shifted to negative potentials, the electron acceptors including potassium ferricyanide and iron cyanocomplexes. Applying the present invention to sensors enables to limit impacts of inhibitory substances and other substances on, e.g., measurements of specific components in biological samples.

This application is entitled to and claims the priority of Japanese Patent Application No. 2010-222142 filed on Sep. 30, 2010, the content of which is herein incorporated by reference in its entirety.

INDUSTRIAL APPLICABILITY

In the present invention, a reagent composition containing an oxidoreductase and an electron acceptor further contains a heterocyclic compound, whereby current changes between before and after storage period are limited. The reagent composition is advantageously used for a reagent layer in a sensor. It is therefore possible to provide more accurate results in electrochemical detection of target substances. The present invention is expected to contribute to further developments of the fields of electrochemical detection of target substances.

REFERENCE SIGNS LIST

1 Sensor
2 Substrate
3 Conductive Layer
31 Working Electrode
32 Counter Electrode
33 Sensing Electrode
4 Reagent Layer
5 Spacer
51 Capillary
52 Inlet
6 Cover
61 Vent hole
100 Sensor System
101 Measurement Section
102 Display Section
103 Mounting Section
104-106 Connector
107 Switching Circuit
108 Reference Voltage Source
109 Current/Voltage Conversion Circuit
110 A/D conversion Circuit
111 Computation Section
112 Power Section
113 Operation Section

The invention claimed is:

1. A sensor comprising:
at least one pair of electrodes; and
a reagent layer being in contact with at least a part of one of the pair of electrodes,
wherein the reagent layer comprises:
a FAD-dependent glucose dehydrogenase;
a quinone or a quinone derivative as an electron acceptor; and
a heterocyclic compound represented by one of the following general formulae (I-1) to (I-5):

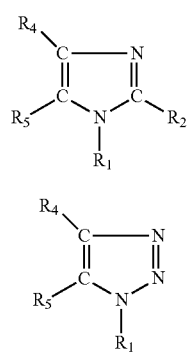

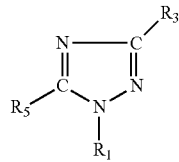

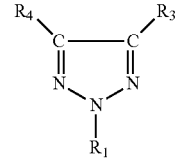

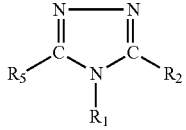

wherein:
$R_1$ represents a hydrogen atom;
$R_2$ to $R_5$, if present, each independently represent a hydrogen atom, an amino group, a hydroxyl group, or a $C_{1-12}$ hydrocarbon group;
the $C_{1-12}$ hydrocarbon group may have at least one substituent selected from the group consisting of an amino group, a hydroxyl group, and a carboxyl group;
at least one of $R_2$ to $R_5$ of the heterocyclic compound is an amino group; and
the heterocyclic compound is not histidine or histamine.

2. The sensor according to claim 1, wherein the electron acceptor is selected from the group consisting of naphthoquinone, anthraquinone, phenanthrenequinone, phenanthroline quinone, and quinone derivatives thereof.

3. The sensor according to claim 1, wherein the heterocyclic compound has five nitrogen atoms.

4. The sensor according to claim 1, wherein the heterocylic compound is at least one compound selected from the group consisting of 2-amino-imidazole, 3-amino-1,2,4-triazole, 4-amino-1,2,4-triazole, and 3,5-diamino-1,2,4-triazole.

5. The sensor according to claim 1, wherein the reagent layer is solid.

6. A sensor comprising:
at least one pair of electrodes; and
a reagent layer being in contact with at least a part of one of the pair of electrodes,
wherein the reagent layer comprises:
a FAD-dependent glucose dehydrogenase;
a quinone or a quinone derivative as an electron acceptor; and
a heterocyclic compound,
wherein the heterocyclic compound is at least one compound selected from the group consisting of 2-amino-imidazole, 4,5-bis(hydroxymethyl)imidazole, 2-methylimidazole, 1,2-dimethylimidazole, 3-amino-1,2,4-triazole, 4-amino-1,2,4-triazole, and 3,5-diamino-1,2,4-triazole.

* * * * *